United States Patent
Emrick et al.

(10) Patent No.: US 7,470,840 B2
(45) Date of Patent: Dec. 30, 2008

(54) LIQUID-LIQUID INTERFACIAL NANOPARTICLE ASSEMBLIES

(75) Inventors: Todd S. Emrick, South Deerfield, MA (US); Thomas P. Russell, Amherst, MA (US); Anthony Dinsmore, Amherst, MA (US); Habib Skaff, Amherst, MA (US); Yao Lin, Amherst, MA (US)

(73) Assignee: University of Massachusetts, Amherst, MA (US)

( * ) Notice: Subject to any disclaimer, the term of this patent is extended or adjusted under 35 U.S.C. 154(b) by 848 days.

(21) Appl. No.: 10/753,868

(22) Filed: Jan. 8, 2004

(65) Prior Publication Data

US 2004/0202682 A1   Oct. 14, 2004

Related U.S. Application Data

(60) Provisional application No. 60/438,628, filed on Jan. 8, 2003.

(51) Int. Cl.
*A61K 33/04*   (2006.01)
(52) U.S. Cl. .................................. 977/787; 424/703
(58) Field of Classification Search ............ 977/787; 424/703
See application file for complete search history.

(56) References Cited

U.S. PATENT DOCUMENTS

| 6,017,390 A | 1/2000 | Charych et al. |
| 2004/0067159 A1 * | 4/2004 | Carnes et al. ................. 422/28 |

OTHER PUBLICATIONS

Lin, Y., Skaff, H., Emrick, T., Dinsmore, A.D., and Russell, T.P., "Nanoparticle Assembly and Transport at Liquid-Liquid Interfaces." Science, Jan. 10, 2003, vol. 299, pp. 226-229.

Nikolaides, M.G., Bausch, A.R., Hsu, M.F., Dinsmore, A.D., Brenner, M.P., Gay, C. and Weltz, D.A., "Electric-field-induced capillary attraction between like-charged particles at liquid interfaces," Nature, Nov. 21, 2002, vol. 420, pp. 299-301.

Dinsmore, A.D., Hsu, M.F., Nikolaides, M.G., Marquez, M., Bausch, A.R., and Weitz, D.A. "Colloidosomes: Selectively Permeable Capsules Composed of Colloidal Particles." Science, Nov. 1, 2002, vol. 298, pp. 1006-1009.

(Continued)

*Primary Examiner*—Raymond J Henley, III
(74) *Attorney, Agent, or Firm*—Reinhart Boerner Van Deuren s.c.

(57) ABSTRACT

Self-assembly of nanoparticles at the interface between two fluids, and methods to control such self-assembly process, e.g., the surface density of particles assembling at the interface; to utilize the assembled nanoparticles and their ligands in fabrication of capsules, where the elastic properties of the capsules can be varied from soft to tough; to develop capsules with well-defined porosities for ultimate use as delivery systems; and to develop chemistries whereby multiple ligands or ligands with multiple functionalities can be attached to the nanoparticles to promote the interfacial segregation and assembly of the nanoparticles. Certain embodiments use cadmium selenide (CdSe) nanoparticles, since the photoluminescence of the particles provides a convenient means by which the spatial location and organization of the particles can be probed. However, the systems and methodologies presented here are general and can, with suitable modification of the chemistries, be adapted to any type of nanoparticle.

31 Claims, 16 Drawing Sheets

OTHER PUBLICATIONS

Dinsmore, A.D., Wong, D.T., Nelson, P., and Hodh, A.G., "Hard Spheres in Vesicles: Curvature-Induced Forces and Particle-Induced Curvature." The American Physical Society, Jan. 12, 1998, vol. 80, No. 2, pp. 409-412.

Bowden, N., Terfort, A., Carbeck, J., and Whitesides, G.M., "Self-Assembly of Mesoscale Objects into Ordered Two-Dimensional Arrays." Science, Apr. 11, 1997, vol. 276, pp. 233-235.

Su, B., Abid, J.P., Fermin, D.J., Girault, H.H., Hoffmannova, H., Krtil, P., and Samec, Z. "Reversible Voltage-Induced Assembly of Au N anoparticles at Liquid-Liquid Interfaces." J.Am. Chem. Soc. 2004. vol. 126, No. 3, pp. 915-919.

Muller, T., Flynn, G.W., Mathauser, A.T., and Teplyakov, A.V., "Temperature-Programmed Desorption Studies of $n$-Alkane Derivatives of Graphite: Desorption Energetics and the Influence of Functional Groups on Adsorbate Self-Assembly." Langmuir, 2003, vol. 19, No. 7, pp. 2812-2821.

Muller, A., Krickemeyer, E., Bogge, H., Schmidtmann, M., Botar, B. and Talismanova, M.O., "Drawing Small Cations into Highly Charged Porous Nanocontainers Reveals "Water" Assembly and Related Interaction Problems." Agnew. Chem. Int. Ed. 2003, vol. 42, pp. 2085-2090.

Yodh, A.G., Lin, K.H., Crocker, J.C., Dinsmore, A.D., Verma, R. and Kaplan, P.D., "Entropically driven self-assembly and interaction in suspension." Phil. Trans. R.Soc. Lond. 2001. vol. 359, pp. 921-937.

Dinsmore, A.D., Crocker, J.C. and Hodh, A.G., "Self-Assembly of colloidal crystals," Current Chemistry, Feb. 1998, vol. 3 No. 1, pp. 5-11.

* cited by examiner

LIQUID-LIQUID INTERFACIAL NANOPARTICLE ASSEMBLIES

This application claims priority benefit from U.S. provisional application Ser. No. 60/438,628 filed Jan. 8, 2003, the entirety of which is incorporated herein by reference in its entirety.

The United States government has certain rights to this invention pursuant to grant no. DEFG96ER45612 from the Department of Energy to the University of Massachusetts.

BACKGROUND OF THE INVENTION

Controlling morphology at the nanometer scale has the potential to revolutionize technology through development of materials with exquisite control of mechanical, optical, electronic and structural properties. Moreover, recent research has led to a host of new fundamental scientific insights, including controlled nanoscale synthesis and processing of both organic (soft) and inorganic (hard) material and the development of nano-scale precursors for macroscopic materials and devices. A challenge, therefore, is to develop a hierarchical approach that can combine a variety of organic and inorganic building blocks, provide nanometer-scale structural control and simultaneously lead to macroscopic devices or materials in a practical and cost-effective way. Moreover, the approach must be flexible so that it can be readily extended to a variety of materials or properties without substantial revision of the entire process. These are demanding goals that require novel approaches and development of basic science.

Photolithography provides a means of generating structure, generally planar in nature, with a spatial resolution on the tenths of micron size scale, but this technique is limited to a small set of materials. Chemical synthesis can provide molecular resolution, but does not provide a robust and flexible method of independently controlling mechanical, structural, electronic and optical properties of a material.

Earlier attempts to synthesize organic/inorganic materials at fluid interfaces involved mesoporous silica or titania at the surface of a water droplet in oil or an oil droplet in water. These structures, however, do not contain well-defined features, nor can the composition of the oil or aqueous phases be altered without substantially changing the inorganic layer. Other approaches to interfacial self-assembly have used millimeter-sized objects with patterned hydrophobicity. This technique, however, has not been extended to the micro- or nano-scale.

Alternatively, electrostatic deposition of alternating layers of polymers or particles or polymerization on the surfaces of small particles or oil droplets provides a flexible route to encapsulation: the capsule is formed around a nanometer-to-micron-sized sphere or a crystal of a water-insoluble material. The capsule can then be swollen and filled from the surrounding phase. Such an approach works for a broad range of materials but the features, specifically pores, are restricted in size to a few nanometers or less and are not well defined in shape. In addition, encapsulation is limited only to water-insoluble objects or objects small enough to be inserted into the swollen pre-constructed capsule from the exterior.

SUMMARY OF THE INVENTION

In light of the foregoing, it is an object of the present invention to provide methods and systems for liquid or fluid interfacial nanoparticulate assembly, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a method and/or system for fluid interfacial nanoparticulate assembly, the resulting structures of which can be nanodimensioned depending upon fluid interface and particulate identity.

It is another object of the present invention to provide a method and/or system for chemical modification of such assembled structures.

It can be another object of the present invention to use such assembled and/or modified structures as intermediates in a range of material applications or synthetic procedures, as delivery platforms for bio or therapeutic agents, or for chemical or physical interaction and associated sensor function.

Other objects, features, benefits and advantages of the present invention will be apparent from this summary and its descriptions of certain embodiments, and will be readily apparent to those skilled in the art having knowledge of fluid interactions and nanoassembly techniques. Such objects, features, benefits and advantages will be apparent from the above as taken into conjunction with the accompanying examples, data, figures and all reasonable inferences to be drawn therefrom.

Figure 2:
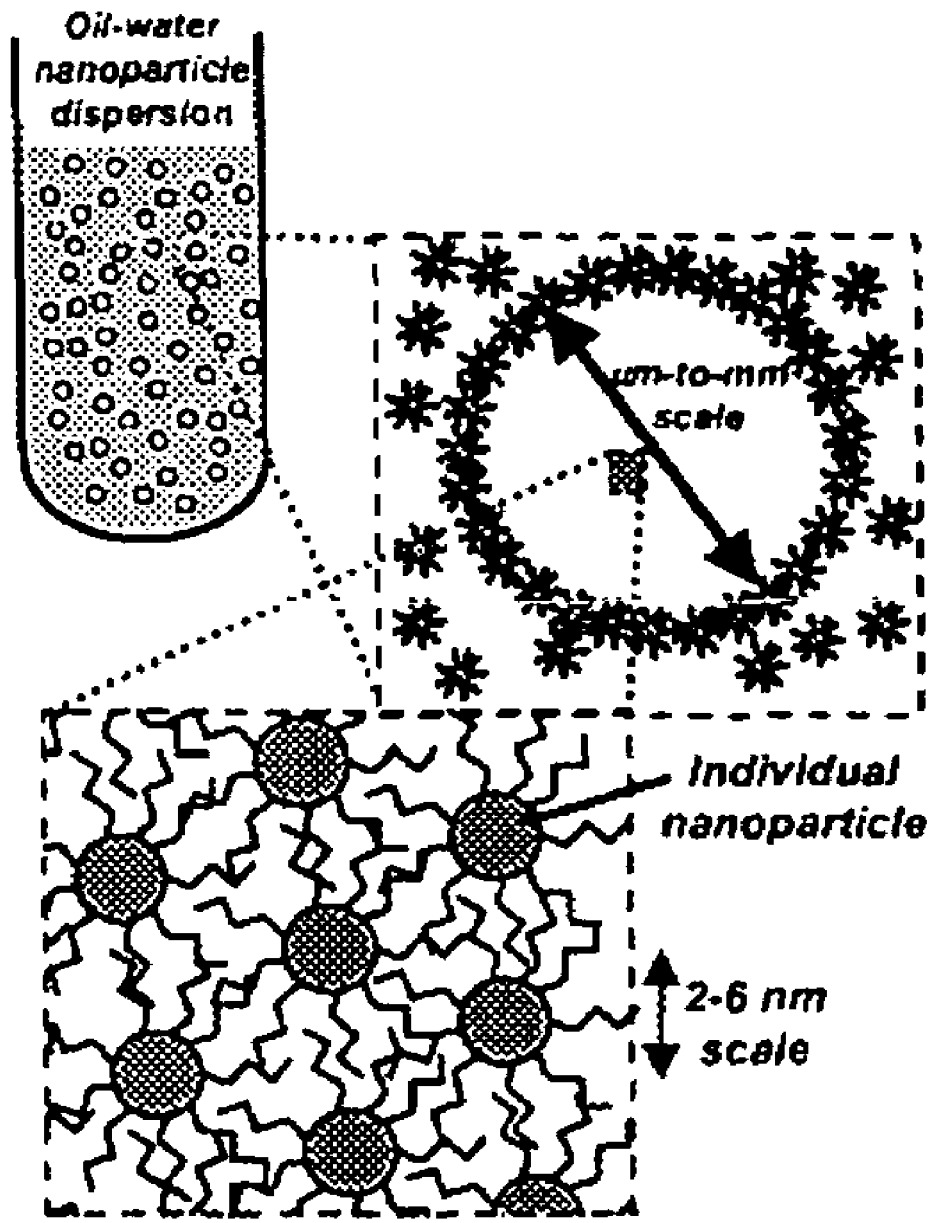
FIG. 2. Another schematic diagram of nanoparticle-coated droplets, in accordance with this invention.

The present invention provides one or more methods related to directed self-assembly of functionalized nanoparticles at a fluid-fluid interface, such as that available using the surface of a dispersed droplet (FIG. 2). This approach provides a unique route to directed assembly of nanoparticles while maintaining the chemical, optical and/or electronic properties of the nanoparticles themselves. A fluid component interface provides easy access to the nanoparticles for subsequent chemical modification, including ligand exchange and crosslinking. The interfacial chemical interactions can be used to produce novel materials for controlled encapsulation and release, filtration and sensing—such capsules whose permeability is controlled with significantly greater precision than is possible with existing technologies. For example, capsules can be brightly photoluminescent with a color chosen according to the contents; they can be magnetic or electrically conducting (and thus act as nanoscopic Faraday cages); they may also be designed for content release under external stimuli.

This invention can be considered in light of two aspects relating thereto: nanoparticles and a fluid-fluid interface between a first fluid component and a second immiscible fluid component dispersed therein or thereby. The nanoparticles of this invention, in certain embodiments preferrably those particles less than or equal to about 100 nm in diameter, are well-suited to the present hierarchical self-assembly techniques, as the nanoparticle "cores" provide optical and/or electronic properties, while surface ligands or associated moieties can affect chemical interactions and/or assembly. The surfaces are chemically modified without significantly altering the nanoparticles' electronic or optical properties, and without aggregation. Certain embodiments of and aspects relating to this invention can utilize CdSe nanoparticles, as their bright photoluminescence is advantageous for characterization; however, a wide variety of nanodimensional materials (e.g., metals, metal oxides, and magnetic nanoparticles) and suitable fluids/solvents may be used with good effect. More generally, nanoparticles can provide an array of uniquely controllable electronic and optical properties, such as electronic band gap, electron transport, optical absorption and photoluminescence spectra, and enhanced nonlinear optical polarizability. Accordingly, such nanodimensioned materials include but are not limited to iron oxides, CdTe, CdS, Au, and Co. Likewise, various core-shell type materials, such as but not limited to CdSe/ZnS, can be used in conjunction with a wide range of available ligand or complexing agents, such materials and ligands as are commercially available or prepared using such known synthetic techniques—as would be understood by those in the art made aware of this invention.

The availability of a fluid-fluid interface also offers unique advantages for assembly and chemical manipulation, as compared for instance to fluid-solid interface systems. The high mobility of particles at fluid interfaces minimizes structural defects, and large crystalline monolayer arrays may be obtained. Reagents and nanoparticles can approach or be approached from both sides of the interface, leading to very facile and rapid interfacial chemistry. Encapsulation can be achieved using crosslinked nanoparticles, with capsule permeability and strength controlled with exceptionally fine precision. The surfaces of dispersed droplets offer substantially more interfacial area than a volumetrically-comparable fluid-solid interface (by a factor of a thousand in a milliliter-sized vessel). Moreover, the size and morphology of droplets can be controlled, with the droplets themselves forming microscopically and macroscopically ordered materials.

This inventive approach offers considerably more control of nanoparticle linking and the physical characteristics of the resulting films or capsules. Moreover, smaller nanoparticle size allows selective permeability over a broader (and more useful) range of macromolecular dimensions. Finally, the electronic and optical properties of the nanoparticles themselves (e.g., photoluminescence, electrical conductivity) provide a route to materials with unique and unusual properties, heretofor unavailable through the prior art.

By way of illustration, nanoparticles suspended in toluene self-assembled at the surfaces of water droplets. A confocal microscope image of a water droplet in toluene containing CdSe nanoparticles coated with tri-n-octylphosphine oxide (TOPO) shows fluorescence from the CdSe nanoparticles, which are preferentially located at the interface. In addition, the adsorbed nanoparticles stabilized the water droplet. Fine dispersions of the water phase are available by sonication or vigorous shaking. Stable water droplets, encased in the CdSe nanoparticles and with diameters ranging from about 0.1 to about 20 microns, were easily achieved. Other samples were prepared by suspending aqueous droplets containing sulforhodamine-B, a water-soluble fluorescent dye. After agitation of this solution in a toluene solution of nanoparticles, the image at 535 nm (CdSe photoluminescence) showed no change. Again the nanoparticles were at the surface of the water droplet. The image at 543 nm, characteristic of the rhodamine dye, showed fluorescence only within the droplets with no fluorescence in the toluene phase. Taken together these data show that the CdSe nanoparticles self-assembled at the water-toluene interface can encapsulate and stabilize the water droplet (FIG. 2).

Without limitation to any theory or mode of operation, the assembly of nanoparticles at the interface may be affected, generally, by the minimization of the free energy $\Delta F$, which is given by $$\Delta F = \Delta H - T\Delta S,$$

where $\Delta F$, $\Delta H$, and $\Delta S$ are changes in the free energy, enthalpy and entropy resulting from the assembly of particles at the interface. Particle assembly causes entropy to decrease on the order of about 1 $k_B$ per adsorbed particle, where $k_B$ is the Boltzmann constant. To minimize the free energy, therefore, $\Delta H$ must be negative. In the absence of particles, the enthalpy is dictated by the water-toluene contacts. When nanoparticles coated with alkane ligands are dispersed in the toluene, $\Delta H$ also depends on the number of alkane-water and alkane-toluene contacts. The water-toluene contacts are least favorable. Thus, by assembling at the interface, the nanoparticles will shield the water from the toluene using the less energetic alkane-water and alkane-toluene contacts. With multiple ligands per nanoparticle, $\Delta H$ will generally greatly exceed $T\Delta S$ in magnitude, and $\Delta F$ can be strongly negative.

Likewise, without limitation to any one theory or mode of operation, interfacial assembly can also be considered in the context of surface tension. The area of contact between the two solvents (water and toluene) is reduced when a nanoparticle resides at the interface. As long as water-oil surface tension exceeds the difference between the particle-oil and particle-water surface tensions, the particles will assemble at the interface. In addition, the overall surface tension of a coated droplet is less than that of the uncoated droplet. It is known, of course, that particles can act as surfactants and stabilize droplets (i.e., "Pickering emulsions"). However, the potential of this invention for controlled structure formation and chemical modification of adsorbed nanoparticles has not heretofor been recognized.

In support of such considerations, alkane-stabilized nanoparticles suspended in hexane did not assemble at the surface of a water droplet. In this system, the solvent is essentially identical to the molecular structure of attached ligand $((-CH_2-)_n)$: replacing water-hexane solvent contacts with water-hexane particle contacts did not reduce enthalpy. Hence $\Delta F$ was very small or positive and, consistent therewith, the particles were not observed to adsorb.

Previously, micron-sized adsorbed particles were observed to provide robust two-dimensional hexagonal ordering on droplet surfaces under a wide variety of conditions. The lateral interactions among particles adsorbed on the droplet surface were found to be a combination of vanderWaals attraction and, over a longer range, dipolar electrostatic repulsion. When the oil-water surface tension was large (as with a mixture of decahydronapthalene and water), an unexpected attraction at separations >5 μm was observed and attributed to capillary forces arising from deformation of the interface by the electric field surrounding the charged particles. However, distinct from the prior art, short-range steric repulsion is expected to stabilize the nanoparticle-ligand complexes of this invention.

The controlled adsorption of functionalized nanoparticles on the surfaces of droplets can be used to develop a variety of chemical ligand-exchange methods, to explore the fundamental mechanisms of particle adsorption on fluid interfaces, and to fabricate a variety of materials. Consideration of the physical and chemical mechanisms underlying the selfassembly process and the interactions among adsorbed nanoparticles can provide improved materials and structures with unique functionality. Various methods of this invention utilize adsorbed nanoparticles to provide a rigid nanoparticle shell. By solvent system choice or exchange, capsules can be designed that have unique and highly controllable toughness, permeability, and optical properties for diverse applications in delivery, filtration and sensing. Multiple ligands or ligands with multiple functionalities can be bound, attached, or complexed with the nanoparticles to promote interfacial segregation and assembly. Specific interactions between nanoparticle ligands and a variety of fluid components are used to enhance the localization of particles at the interface and to control surface density.

As mentioned above, cadmium selenide nanoparticles are used with certain embodiments, as their photoluminescent properties provide a diagnostic means to probe spatial location and assembly. However, the present invention, in its broader context can, with suitable modification of the associated chemistries, be adapted to diverse nanoparticle types (including metallic, magnetic, and insulating compounds) and a wide variety of solvent or fluid components (including buffered aqueous solutions that are compatible with bioactivity).

Nanoparticle-based materials, especially those with active electronic and luminescent properties, have attracted a great deal of interest as components in biotechnology related applications, especially for use as fluorescent tags for diagnostics and detection. These inorganic semiconductor nanoparticles, or quantum dots (QD's), are advantageous relative to organic fluorophores in that they show good resistance to photobleaching and possess very narrow emission profiles. In addition, nanoparticles of different size and therefore different emission wavelength can be excited continuously above the bandgap. Opportunities are thereby provided for complex biological studies based on this precise detection mechanism, as a single source of white light irradiation can produce multiple emission colors.

Solubilization of nanoparticles in aqueous media is a prerequisite to many biological applications, and current research in the field requires laborious, multi-step synthetic procedures to obtain water-soluble nanoparticles with good stability. For example, the prior art demonstrated that CdSe/ZnS core-shell nanoparticles can be made water-soluble by encapsulation with a silica shell containing ionizable endgroups. Techniques adopted in other laboratories have relied on organic encapsulants, usually hydrophilic water-dispersing thiols, to solubilize the CdSe nanoparticles in aqueous media. Such approaches are rapid, but give nanoparticles with lower stability, and pH dependent water solubility. In the context of CdSe with thiol coverage, disulfide formation ultimately leads to nanoparticle instability.

Figure 3:
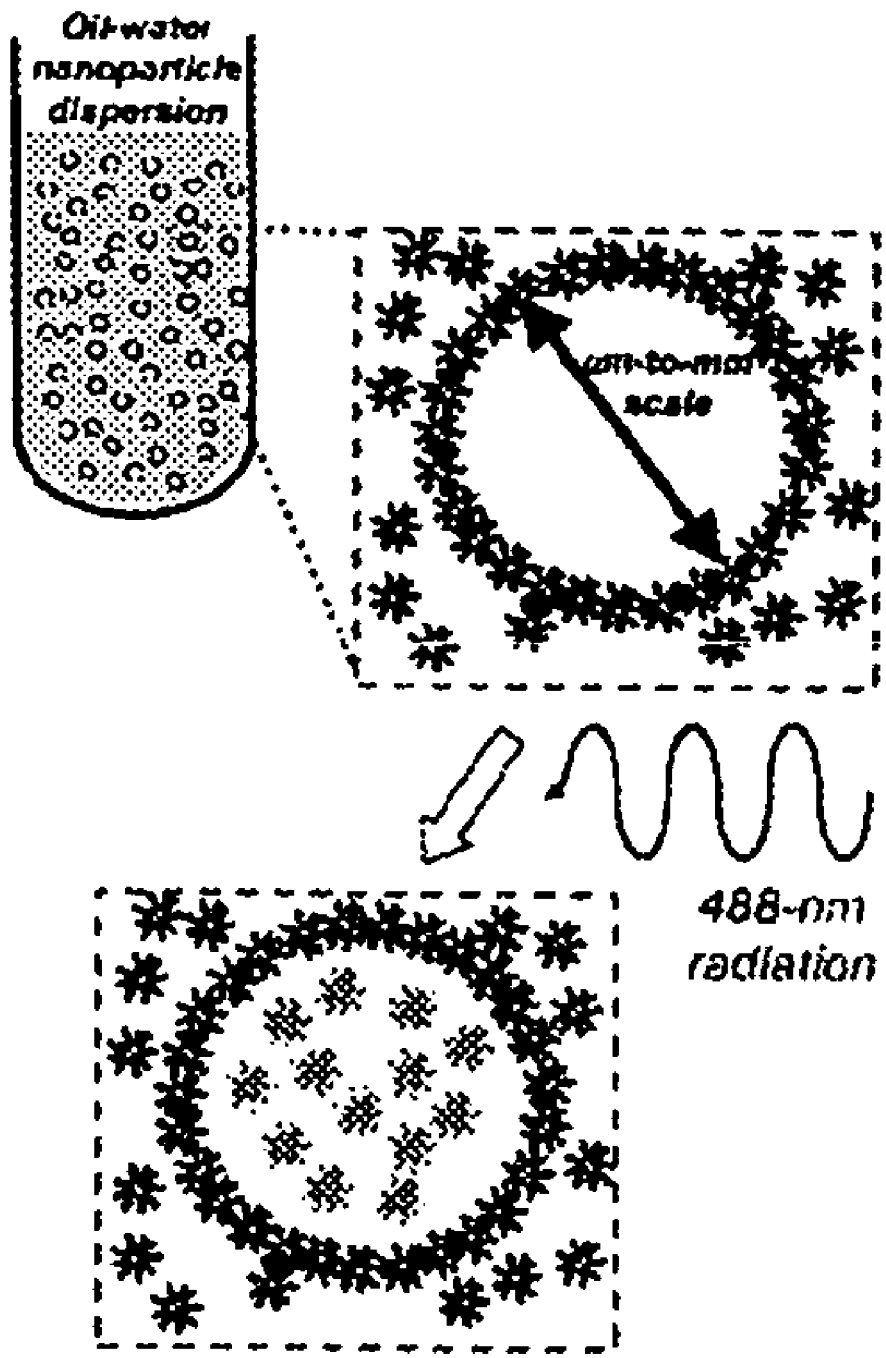
FIG. 3. Another schematic diagram of phenomenon observed, in accordance with certain embodiments of this invention.

As a fortuitous aspect of this invention, interfacial ligand-exchange reactions can be used en route to other embodiments of this invention, one of which provides an in situ, nominally or optionally one-step, process by which hydrophobic ligands may be replaced by hydrophilic ligands and nanoparticles may be transferred from an oil/organic to an aqueous phase. Thus, multistep reactions of the prior art to produce water soluble nanoparticles can be replaced with a simple interfacial exchange reaction. As illustrated with the aforementioned CdSe system, the bright photoluminescence of the CdSe nanoparticles was retained after transfer to water. As provided in several examples below, water droplets containing dissolved sulforhodamine-B dye were coated with a self-assembled layer of CdSe nanoparticles. After irradiation with 488-nm light for several minutes, the nanoparticles transferred from the interface into the aqueous phase (see, schematically, FIG. 3). This remarkable transfer was observed to occur when the dye was present in the aqueous droplet. With pure-water droplets, i.e., with no dye present, the particles remained at the interface after continued irradiation. Thus, a photoinitiated ligand exchange has occurred, whereby a sufficient percentage of the TOPO ligands that are coordinated to the CdSe nanoparticle are displaced by, or have reacted with, the hydrophilic dye.

As such, this invention represents a simple, direct process by which water-dispersed nanoparticles can be obtained starting with the conventional oil-soluble (e.g., tri-n-octyl phosphine oxide (TOPO)-covered/complexed) nanoparticles. No special preparation of water-soluble surface ligands is required; rather, water-solubility is obtained by an interfacial process, in conjunction with irradiation at a suitable wavelength or frequency depending on a given nanoparticle/ligand complex system. In this interfacial process, the nanoparticles, perhaps driven by a reduction in the interfacial energy, assemble at the oil-water interface, and upon exposure to irradiation, are transported across the oil-water interface to the water phase. Fluorescent confocal microscopy shows that the nanoparticles are photoluminescent in both the oil-soluble and water-soluble states. While this inventive aspect is illustrated using CdSe nanoparticles, due to their convenient photoluminescent and thus easily probed properties, it can be adapted in a straight-forward manner to any ligand-stabilized nanoparticle with suitable modification of the chemistries.

The observed interfacial transfer involves assembly of luminescent CdSe nanoparticles (e.g., about 2 nm to about 10 nm diameter spheres) at the interface between two immiscible fluids (i.e., anorganic fluid and water). As shown below, while these nanoparticles are stable at the oil-water interface, and indeed stabilize the interface, continued irradiation of the system with 488 nm light (argon ion laser) results in water solubilization of the nanoparticles. Without limitation, chemical reagents present in the water phase (e.g., organic dyes containing reactive functionalities) can interact with the nanoparticles and/or act as stabilizing ligands upon irradiation, making the surface hydrophilic and allowing entry into the water phase.

Within the broader context of this invention, such assembly and transfer can be varied according to the nature of the organic phase, the contents of the water phase, the types (i.e., sizes and compositions) of nanoparticles, and the ligands on the nanoparticles—all of which can provide system flexibility and impact applications related to this interfacial transport and water solubility of the nanoparticles.

Figure 1:
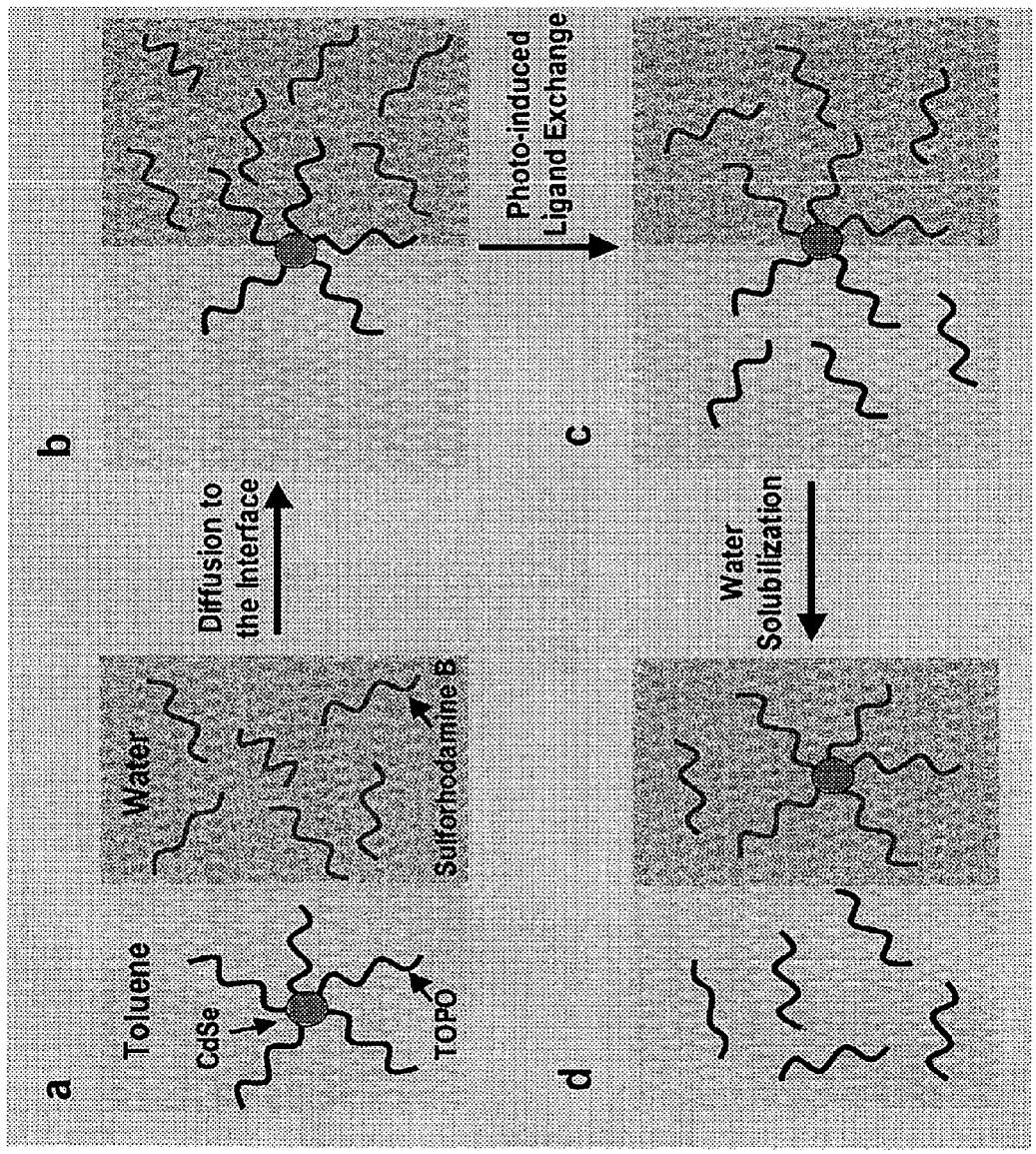
FIG. 1. Schematic illustration of a possible mechanism of nanoparticles transferring from oil to water.

Without theoretical or mechanistic limitation, the data associated with the aforementioned embodiment suggest that the sulforhodamine-B adsorbs onto the CdSe nanoparticles surface, possibly through the sulfonate groups, upon irradiation. This is shown schematically in FIG. 1. Regardless of the mechanism, this method presents a very direct route to produce photoluminescent, water soluble nanoparticles, using the conventional oil-soluble nanoparticles as the starting material.

Accordingly, the present invention provides, in part, a system for assembly of nanoparticles. Such a system comprises (1) a first fluid component; (2) a second fluid component at least in part immiscible with the first component and dispersed thereby; and (3) a nanoparticulate component interfacially contacting the first and second fluid components. Such a particulate can comprise a variety of materials or compositions of the sort described herein. Certain embodiments comprise a substrate with at least one ligand and/or interacting moiety thereon, associated therewith and/or complexed thereto. Such nanoparticulate substrates and ligand moieties can include those described herein or as would otherwise be known to those skilled in the art and made aware of this invention, the choice or design thereof limited only by way of 1) the aforementioned entropy, enthalpy and/or surface tension considerations, 2) the solvation or dissolution thereof by the first or second fluid component, and/or 3) the ability of such substrate components to assemble on, or come into contact with, the second immiscible, dispersed fluid component of such a system.

Nanoparticulate composition can be used to vary particulate diameter, such dimension limited only by the fluid/fluid interfacial assembly of such particles and/or resulting fluid component stabilization. Accordingly, the fluid components of this invention can comprise nanoparticulates of varying diametral dimension. As illustrated below, displacement of smaller nanoparticles by those of larger diametral dimension can be related to observed changes in structure and/or performance characteristics (e.g., density, permeability, etc.) of the resulting assembly. With regard to ligands, such a component can without limitation be selected from a hydrophobic or a hydrophilic moiety, depending upon the fluid component within which it is presented. Likewise, a second fluid component, at least partially immiscible with a first fluid component, can further comprise a ligand component, whether hydrophilic or hydrophobic, for subsequent reaction or interaction with the aforementioned nanoparticulate. Reference is made to several of the following examples illustrating ligand exchange, as well as preparation and use of several representative janus particles.

In various embodiments, a substrate component can be used in conjunction with a plurality of ligand/moieties having a reactive functional group, or with one or more ligands having a plurality of reactive functionalities, such functionalities as can be used for inter-ligand coupling or crosslinking. Optionally, the second dispersed fluid component can further comprise alternate ligand moieties and/or molecular components for ligand coupling: The former for ligand exchange and/or modified first/second fluid component solubility, and the later for ligand crosslinking under suitable reaction conditions. Regardless, such inter-ligand crosslinking can provide a capsule assembled on the fluid-fluid interface, as described below, such structures having a size and density as can be controlled by the volume of the dispersed fluid component, nanoparticulate diametral dimension and ligand molecular weight. Capsule pores can be provided by incorporation of nanoparticulates that are inert, unreactive or unaffected under a given encapsulation technique, followed by selective removal of these unreacted components from the capsule structure.

As an extension of such a system, the present invention also includes a method of using a dispersed fluid component for interfacial assembly. Such a method comprises (1) providing a first fluid component; (2) dispersing with the first component a second fluid component at least in part immiscible therewith; and (3) contacting a nanoparticulate at an interface of the fluid components. As described above, such a particulate comprises a substrate composition or material and at least one ligand component moiety thereon, associated therewith and/or complexed thereto. The dimension and identity of such a substrate and/or component moiety are limited only by way of the aforementioned energy-related or functional considerations, leading to assembly of such nanoparticulates on and/or about the second fluid component.

Incorporation of suitable ligand/moieties within the dispersed fluid component can under suitable conditions induce ligand exchange, transfer particulates from one fluid component to another, and/or promote formation of Janus-type particles, defined as a particle with two distinct regions, or hemispheres, of functionality. Subsequent fluid component removal and/or isolation of such nanoparticulates can be used, as described below, in conjunction with suitable monomeric components, in the preparation of block copolymers. Alternatively, incorporation of a suitable ligand/moiety within the dispersed second fluid component can be used to modify nanoparticulate chemistry and/or solubility. For example, in certain embodiments, the nanoparticulate material or composition, while initially soluble in the first (e.g., oil/organic) fluid component, becomes soluble in the second dispersed (e.g., aqueous) fluid component under suitable ligand exchange or reaction conditions.

The phenomenon of water condensing on a clean surface to form well-ordered arrays of droplets has long been observed. The transfer of such structures to polymer surfaces by in-situ condensation of water droplets onto a drying polymer solution has been shown to be a convenient means to "imprint" highly ordered honeycomb structures into polymer films.

Homopolymers and block copolymers, with and without surfactants, have been used to obtain arrays of cavities or holes, so-called "breath figures," with controlled size and separation distance. Use of such arrays for technical applications, e.g. as sensors, filters or catalytic sites, typically requires functionality at the hole surface. In-situ functionalization would be limited to polymeric or low molecular weight surfactants that are amenable to breath figure formation. The introduction of more complex surface structures requires ex-situ functionalization. Ex-situ processing of polymers or low molecular weight surfactants to control the surface properties is made difficult by the limited accessibility of the functional groups embedded in the polymer matrix, as well as the complex chemical reactions involved in generating new functionalities. Demonstrating another aspect of this invention, ligand-stabilized nanoparticles can be used to functionalize such an array of breath figure holes. Such functionalization can provide subsequent ex-situ surface modification by simple ligand exchange in accordance with the method(s) and system(s) described herein.

Figure 15:
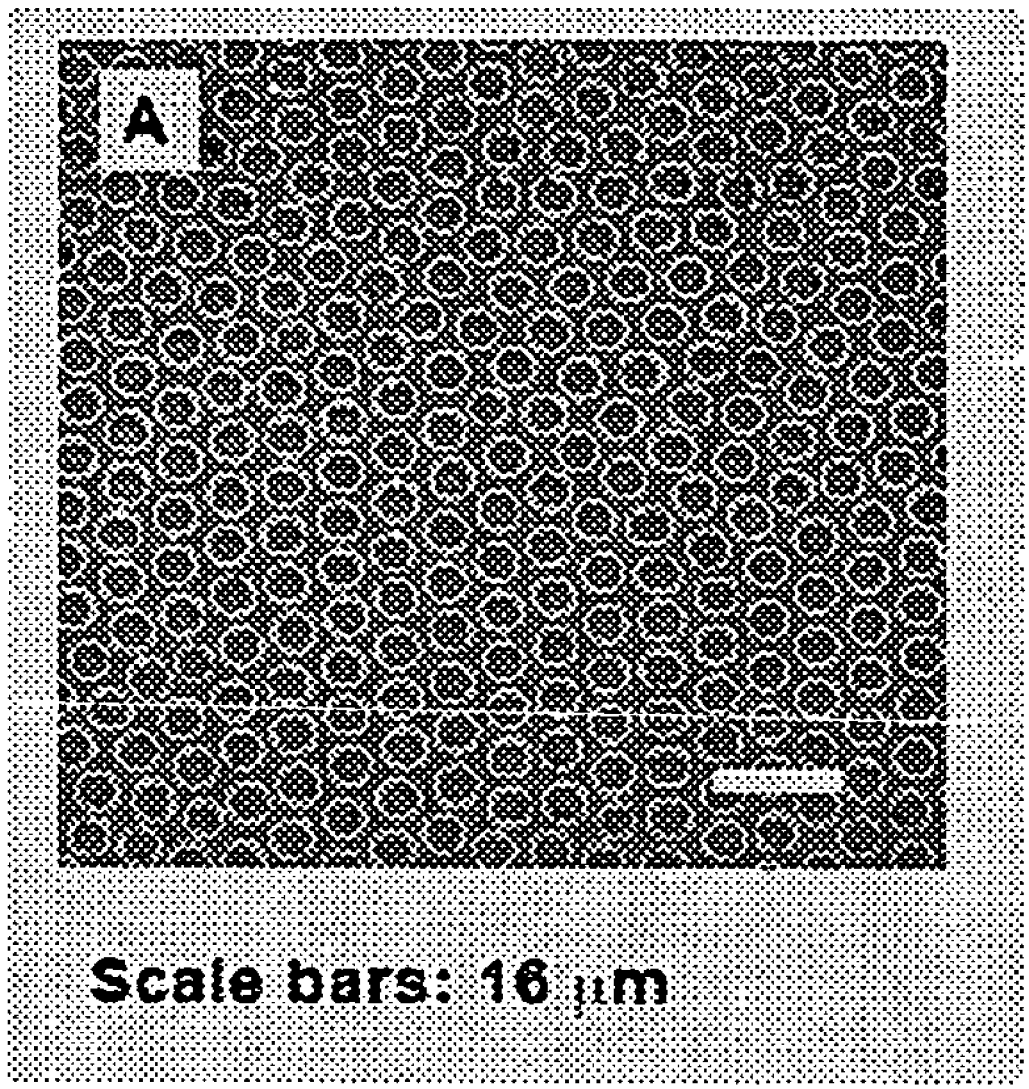
FIG. 15: Optical microscope images of different areas of a sample obtained from solvent casting a polymer film from a 7 wt.-% PS (76 k) solution in chloroform with 1 wt.-% 4 nm TOPO-covered CdSe nanoparticles at 80% humidity. Scale bar: 16 μm.

With reference to several of the following examples, the array of holes/cavities can be prepared by casting a chloroform solution of polystyrene and CdSe nanoparticles in a humidity-controlled chamber. As indicated above, other fluid polymeric solutions and nanoparticles can be used with comparable effect. Solvent evaporation decreases the air-liquid interfacial temperature below the dew point of water, resulting in condensation of water droplets on the polymer solution surface. After nucleation, condensation-limited growth of the droplets results in a narrow droplet size distribution. At a certain average size they order into a hexagonal lattice. If the critical size is exceeded as a result of excessively rapid condensation, the droplets coagulate and the droplet size and size distribution increase dramatically. As the concentration of the polymer/nanoparticle mixture increases with solvent evaporation, the film passes through the glass transition of the polymer and locks the droplets in place. Finally, the water evaporates to yield an array of nanoparticle-decorated holes. FIG. 15 provides a digital optical micrograph image of an array generated by chloroform evaporation from a 7 wt.-% solution of polystyrene containing 1 wt.-% TOPO-covered CdSe nanoparticles (core diameter: 4 nm) at a relative humidity of 80%. The evaporation rate of the solvents and humidity can be adjusted such that the resulting droplet size is varied between 3 and 5 µm.

Figure 16:
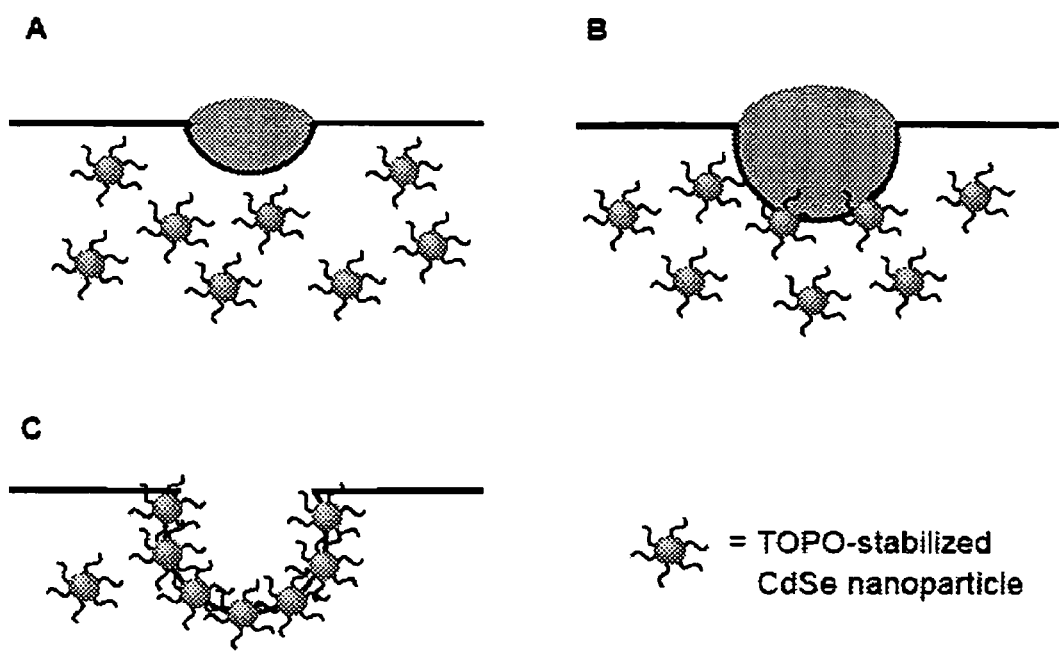
FIG. 16 A-C: Schematic illustration of nanoparticle assembly at a droplet surface during breath figure/array formation (cross section). (A) A small water droplet condenses onto the nanoparticle/polystyrene solution and (B) sinks into the film while the particles segregate to the resulting liquid-liquid interface. (C) After complete evaporation of the solvent, the nanoparticles are positioned at the polymer film-air interface thus functionalizing the surface of the holes.

Stabilization of the growing droplets is believed achieved by nanoparticle assembly at the liquid-liquid, i.e. polymer solution-water droplet interface. In the case of breath figure formation from a polymer/nanoparticle solution, the condensed water droplets can serve as templates for the nanoparticle assemblies. Before the polymer film reaches a certain viscosity, the TOPO-stabilized CdSe particles segregate to the fluid interface and form a uniform layer as depicted schematically in FIG. 16. After evaporation of the solvent the particles are positioned, functionalizing the surface of the remaining holes or cavities, permitting an ex-situ investigation or modification of the resulting structure. A confocal fluorescence microscopic image of a dried polystyrene/nanoparticle film shows, for instance, higher fluorescence intensity at the edge of the cavities indicating that the particles have been trapped near the walls of the spherical cavities, i.e., at the polymer-air interface within the holes.

As is evident from the data presented below, a method/system is presented wherein an array of cavities can be imprinted into a polymer film, the walls thereof decorated with nanoparticles. Modification of the ligands attached to the nanoparticles opens a simple route to functionalize the polymer surface in-situ and tailor the ligands to further optimize the droplet stabilization and thus enhance the overall array ordering. As with other embodiments of this invention, the trioctylphosphine oxide ligands demonstrated can easily be replaced by several moieties including without limitation pyridine, substituted pyridines (i.e., acrylate and polyethylene glycol), thiols, thiophenols, phosphonic acid derivatives, functionalized phosphine oxides (i.e., acrylate, polyethylene glycol and polymerization initiators and/or mediators) and/or ligands with a variety of functional groups optimal for a range of ex-situ surface modification depending upon end use application.

EXAMPLES OF THE INVENTION

The following non-limiting examples and data illustrate various aspects and features relating to the systems, compositions, structures and/or methods of the present invention, including the interfacial assembly and use of nanoparticulate materials, as are available herewith. In comparison with the prior art, the present methods and systems/structures provide results and data which are surprising, unexpected, contrary to, and distinct from, the prior art. While the utility of this invention is illustrated through the use of several nanoparticulate substrates/ligand moieties and fluid component systems, it will be understood by those skilled in the art that comparable results are obtainable with various other nanoparticulate materials and fluid components, as are commensurate with the scope of this invention.

Example 1a

Preparation of TOPO-covered CdSe nanoparticles. Cadmium acetate dihydrate (0.15 g, 0.56 mmol) and tri-n-octyl phosphine oxide (7.5 g, 0.019 mol) were loaded into a three-neck round bottom flask equipped with a thermocouple and condenser. Argon was purged through for 10 min, and the reagents were heated to 320° C. under an $Ar_2$ atmosphere until a clear solution was formed. The temperature was reduced to 300° C. and a solution of Se (0.22 g, 2.8 mmol) in tri-n-octyl phosphine (4.8 mL) was rapidly injected into the reaction mixture. The temperature was reduced to 270° C. and held there until the desired nanoparticle size was achieved. The reaction was allowed to cool to 60° C. and 10 mL of anhydrous methanol were added in order to precipitate the nanoparticles. The nanoparticle and methanol dispersion was subjected to centrifugation so as to isolate the nanoparticles from excess tri-n-octyl phosphine oxide. The nanoparticle were redissolved in tetrahydrofuran and precipitated again with methanol and centrifugated. This process was repeated one more time to ensure removal of excess ligands are removed from the nanoparticle. The nanoparticles were then dissolved in toluene and stored in the dark.

Example 1b

Preparation of CdSe Nanoparticle Assemblies. To a solution (c.a. 2 mL) of TOPO-covered or p-vinylbenzyl-di-n-octylphosphine oxide-covered CdSe nanoparticles in toluene was added one drop of water. The two-phase mixture was mechanically agitated or sonicated to form CdSe nanoparticle stabilized droplets of water in toluene. Both mechanical agitation and sonication techniques lead to assembly but the sonication at frequencies known in the art gives smaller droplets compared with those formed by mechanical agitation.

Example 1c

A fluorescence confocal microscopic image shows a ~20 μm diameter water droplet dispersed in toluene containing 2.8 nm diameter CdSe nanoparticles stabilized with TOPO ligands. The image shows the fluorescence from the CdSe nanoparticles (excitation: 488 nm; emission: 525 nm). Each image is an optical cross-section taken at 2.7 μm intervals in depth through the droplet. Taken together, these data show that the droplet is spherical and that the CdSe nanoparticles segregate to the toluene/water interface, stabilizing the droplet. The observed thickness of the fluorescent ring, on the order of 1 μm, is much larger than the real thickness of the layer, due to a distortion of the images by the droplet shape. In the absence of the nanoparticles, the water droplets were unstable and coalesced. Nanoparticle-coated water droplets with diameters ranging from 10 to 100 microns were obtained simply by shaking; smaller droplet diameters can be obtained by sonication. A fluorescence image was obtained of a similar sample where sulforhodamine-B, a fluorescent dye, was initially dissolved in the water. The CdSe nanoparticles and sulforhodamine-B were independently examined by observing their respective photoluminescence at 525 nm and fluorescence at 585 nm. The CdSe nanoparticles segregate at the toluene/water interface, and the sulforhodamine-B dissolved in the water phase is fully encapsulated by the nanoparticles. No evidence for CdSe in the water phase was observed, as expected from the hydrophobic nature of the n-octyl groups of the TOPO ligands.

Example 2a

As discussed more fully above, interfacial nanoparticle assembly is promoted by reducing the interfacial free energy. Placement of one nanoparticle at the interface will decrease the entropy by $\sim k_B T$. Consequently, $\Delta H$ must be negative to reduce the total free energy. There are three contributions to the interfacial energy arising from the particle/oil interface ($\gamma_{P/O}$), the particle/water interface ($\gamma_{P/W}$) and the oil/water interface ($\gamma_{O/W}$). The energy change, $\Delta E$, due to the assembly of particles at the oil/water interface will depend upon the magnitudes of the interfacial energies and the radii of the particles, R. This energy change is given by $$\Delta E = E_{P/O} - E_{min} = \frac{\pi R^2}{\gamma_{O/W}} \cdot (\gamma_{O/W} - \gamma_{P/W} + \gamma_{P/O})^2.$$

Based on published values for $\gamma_{O/W}$=35 mN/m and estimates of $\gamma_{P/O}$~5 mN/m and $\gamma_{P/W}$~25 mN/m, $\Delta E$~5$k_B$T, for 2.8 nm diameter particles. Since $\Delta E$ depends upon $R^2$, the smaller the nanoparticles, the less stable will be the assembly. In fact, no droplet stabilization was droplet was observed under such conditions using particles with a diameter less than ~2 nm.

Example 2b

Demonstrating the principles of the preceding example, the residence time of a nanoparticle at a fluid interface increases with increasing particle size. Thus, unlike larger, micrometer-sized particles strongly held at an interface, it is possible for smaller nanoparticles to be interfacially displaced with larger particles. For instance, 4.6 nm particles in toluene were introduced to a dispersion containing water droplets in toluene previously stabilized with 2.8 nm particles. Fluorescence confocal microscopic images showed size-dependent displacement of the smaller particles, two-dimentional phase separation of the fluid components, and assembly of the larger particles at the fluid interface. Spontaneous escape of the 2.8 nm nanoparticles is consistent with the energy considerations discussed in the preceding example.

Example 3

Chemical interaction of the nanoparticles at the interface with sulforhodamine-B dissolved in the aqueous phase occurred after repeated scanning of the stabilized water droplets. Initially, results are obtained showing the segregation of the CdSe nanoparticle at the interface. However, over time, the CdSe nanoparticles cross the toluene/water interface and become dispersed in the water phase. However, the fluorescence from the sulforhodamine-B is always restricted to within the droplet, though the fluorescence intensity decreases with time. As seen, there is a segregation of the nanoparticles to the interface and the water phase is still entrapped by the nanoparticle layer. However, photoluminescent nanoparticles are also seen within the water phase. In the absence of the sulforhodamine-B, transfer of the nanoparticle across the water/toluene interface does not occur and the nanoparticles are excluded from the water phase. Upon extended exposure to 488 nm light, the initial hydrophobic (toluene-soluble) TOPO stabilized nanoparticles were converted to hydrophilic (water-soluble) particles.

Example 4

Insight into a possible reaction mechanism is found by monitoring the fluorescence from the nanoparticles (525 nm) and from the dye (585 nm). The former is seen to increase within the droplet until it reaches a plateau, whereas the latter, only seen within the droplet, decreases with time. This observation is not due to a shift in the emission spectrum of the sulforhodamine-B after irradiation. The emission spectrum within the droplets was monitored in situ and no significant shift of the characteristic emission band was observed. Control experiments on droplets of water containing the dye did not show significant photobleaching under identical conditions.

As observed, reduction in the sulforhodamine-B fluorescence occurs only in the presence of the nanoparticles. It is at least inferred that interactions between the dye and the nanoparticles enhance the photobleaching rate of the dye. Plausible mechanisms for such an in situ hydrophobic/hydrophilic transformation include adsorption of one of the dye's functional moieties, i.e. the sulfonate or diethylamonium, to the nanoparticle surface. Adsorption of dye molecules to the nanoparticle surface via the cationic site would produce a hydrophilic sulfonate periphery leading to water solubility. This could occur upon the generation of negative charge on the nanoparticle surface due to the presence of phosphonic acid surfactants and would be consistent with previously proposed surface-induced photooxidation pathways reported for sulforhodamine-B on titanium dioxide and cadmium sulfide surfaces.

Example 5

Structural characterizations. While both fluorescence spectroscopy and fluorescence confocal microscopy have proven to be indispensable in uncovering the assembly of CdSe nanoparticles at the toluene-water interface, they do not provide information on the nanometer length scale. Consequently, small-angle and wide-angle x-ray (SAXS and WAXS) are performed on nanoparticle stabilized water/toluene dispersions. Dispersions are prepared by mechanical agitation or sonication of toluene-H$_2$O, where CdSe nanoparticles have been dispersed in the toluene. The electron density differences between the CdSe and the toluene and water are sufficiently large such that the scattering contains contributions from the interferences arising from the spatial distribution of the nanoparticles assembled at the interface, the form factor of the nanoparticles (very slight angular dependence), the shape of the dispersed phase (restricted to very small angles), and the diffraction from the crystal structure of the CdSe in the nanoparticles. Each of these contributions is separated easily from the scattering profiles and consequently provides a detailed picture of the packing of the nanoparticles at the interface. Small angle neutron scattering (SANS) is used to complement the SAXS and WAXS studies. Experiments using isotopically substituted water and/or toluene (or other oil) are used to further elucidate the organization of the nanoparticles at the interface and the distribution of the nanoparticles in the entire system. Cadmium, unlike many other elements, has a very strong neutron attenuation coefficient and as such provides an effective marker of the nanoparticles. Such studies and data provide an understanding of the particle packing at the interface and the spatial distribution of particles normal to the interface.

Example 6

Transmission and scanning electron microscopy (TEM and SEM) provide real-space images of the particle assemblies at the fluid-fluid interface. Several methods are used to prepare specimens for electron microscopy. Samples are frozen rapidly in liquid propane, then cryo-microtomed and transferred cold into the TEM and SEM. The high electron density of the CdSe nanoparticles, in comparison to the toluene and water, provide more than sufficient contrast to observe the particles.

Example 7

Other procedures are used to prepare the assemblies for observation with electronic microscopy. The dispersed phase can be isolated and examined at room temperature. For instance, an agarose gel can be dissolved in the interior (water) phase and solidified. Subsequently, the exterior phase (toluene) is removed, leaving behind the encapsulated gel. Preliminary confocal microscopy studies indicate that the dispersed water phase remained intact.

To further the objectives of this example, dispersions of styrene in water can be examined. Toluene and styrene are structurally quite similar, but chemically different in that styrene is prone to polymerization. The styrene is polymerized by either thermal or free radical methods to freeze in the styrene phase. Because the assembly of the nanoparticles at the interface appears driven by enthalpy, the polymerization event should not change the assembly of the nanoparticles significantly and the nanoparticles at the interface are embedded in glassy polystyrene. Fractured surfaces or microtomed sections are studied by TEM and SEM to probe particle assembly at the interface.

Example 8

Figure 4:
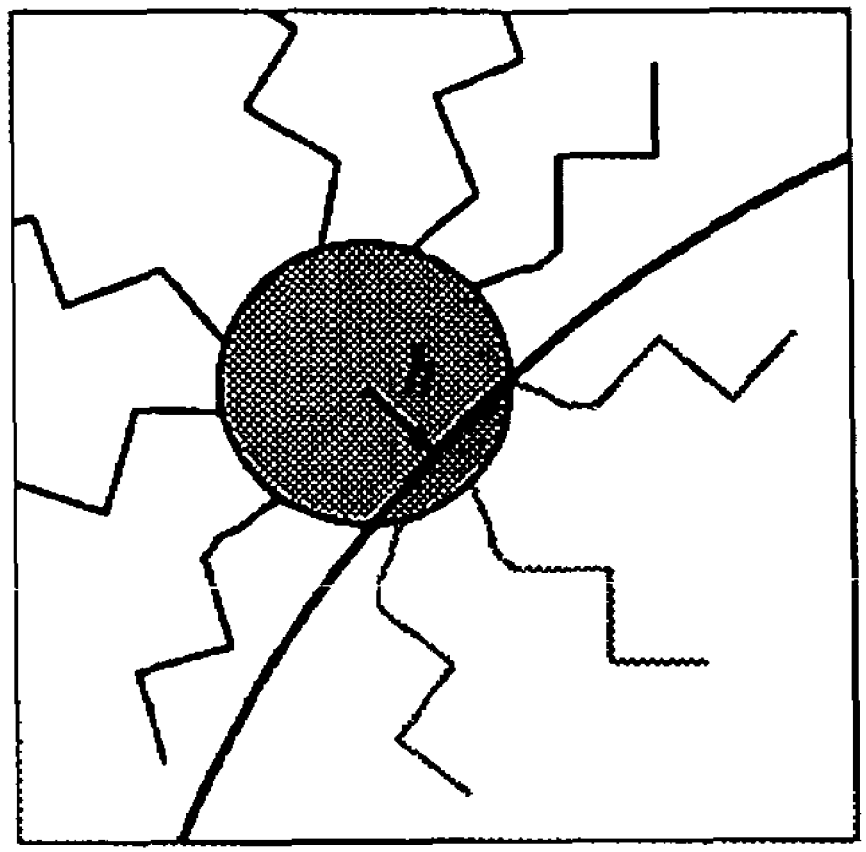
FIG. 4. The depth of penetration of a nanoparticle into the droplet may depend at least in part on the relative surface tensions. h is the distance between the particle center and the plane of the wetting ring.

The position of the nanoparticles with respect to the interface (i.e., the depth of their penetration into the droplet) is measured. Control of depth is needed for the preparation of "Janus" particles, described below. The depth at which the nanoparticles sit at the interface (h) is controlled by the three surface tensions (FIG. 4). Minimizing the energy leads to a simple prediction: h=R ($\sigma_{pi}-\sigma_{pe}$)/$\sigma_{ei}$, where R is the nanoparticle radius, $\sigma_{pi}$ ($\sigma_{pe}$) is the energy per area of the interface between the particle and the interior or exterior fluid, and $\sigma_{ei}$ is the energy per area of the interior-exterior fluid interface. The nanoparticles adhere to the interface if −R<h<R. For many functionalized particles, $\sigma_{ei}$ is much larger than either $\sigma_{pi}$ or $\sigma_{pe}$, and this constraint is met. The depth can be controlled with $\sigma_{ei}$ by changing the temperature, pH, or by addition of other solvents, etc.

Example 9

Surface tension measurements. The presence of nanoparticles at the interface and the ligand-exchange reactions are monitored by measuring the effective surface tension over time. During adsorption of the nanoparticles onto a droplet, the surface tension decreases from its initial value of approximately 10-50 mN/m. The change in surface tension is proportional to the density of adsorbed particles, hence the rate of adsorption and the terminal density may be measured as functions of particle concentration, surface tensions, and nanoparticle and ligand sizes. After the interface is saturated (or after non-adsorbed nanoparticles are washed away from the exterior phase), the surface tension slowly changes as the surface ligands are replaced from the interior phase or are altered photochemically. After washing away excess nanoparticles, the surface tension of a single droplet is measured over a period of hours to monitor the progress of interfacial reactions. The results of this example can be compared with structural characterizations from preceding examples.

Samples can be characterized as a function of time, solvent type, the sizes and concentration of dispersed nanoparticles, the temperature of the dispersion, and the sizes of the droplets. High quality CdSe nanoparticles (true nanocrystals with low polydispersity) with diameters ranging from about 1- to about 8 nm are prepared and used for such characterizations.

Example 10

Figure 5:
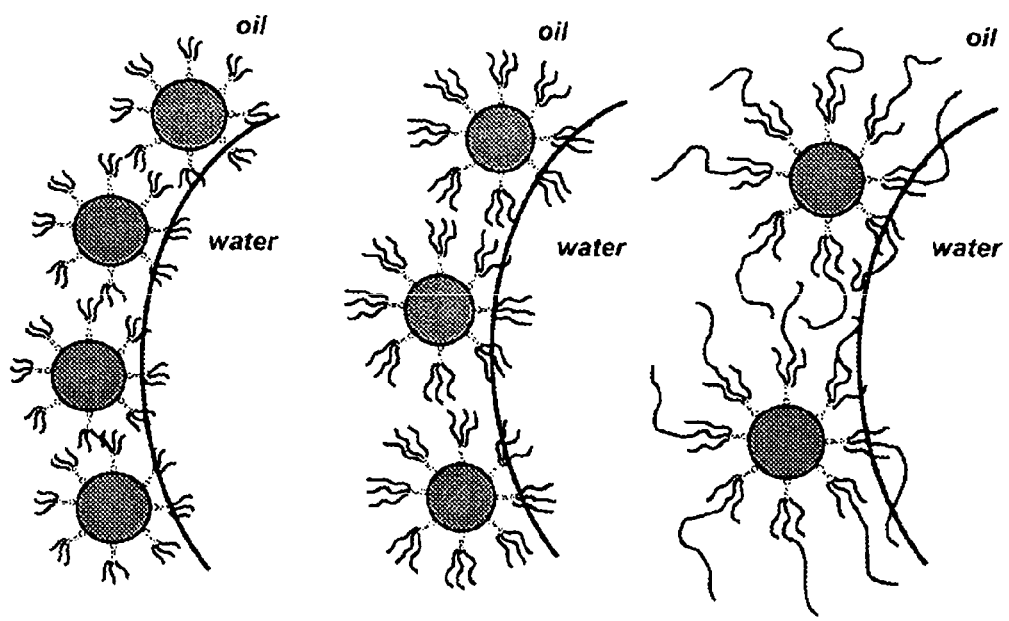
FIG. 5. Expected changes in interfacial density of nanoparticles at interfaces with increasing ligand size from left to right.

Effect of ligand size and structure on interfacial nanoparticle density. The effect of ligand size on inter-nanoparticle spacing has been investigated for nanoparticle superlattices, where increased spacing was observed for nanoparticles encapsulated with C-8 hydrocarbons relative to C-4 hydrocarbons. The present invention can utilize such control over nanoparticle packing or spacing to design and tune surface density of nanoparticles at an oil-water interface (FIG. 5). The size of the nanoparticle encapsulating ligands, and hence nanoparticle density, are varied by changing the length of the alkyl chains on phosphine oxide or other ligands. Polymers of substantial molecular weight (from about 5000 to about 20,000 g/mol) can be grown directly from these ligands, radially outward from the nanoparticles. Like their TOPO-covered counterparts, these polymer-functionalized nanoparticles are hydrophobic in nature, also capable of assembly at the interface. Polymer-CdSe and other nanoparticulate composites of this invention comprise fully saturated aliphatic polymers (e.g., polyethylene, polymethylmethacrylate, polystyrene, polyalkylene oxides and polyisoprene), as well as a range of saturated aliphatic-based polymers. Regarding the latter, unsaturation (e.g., double bonds) may be useful for preparing crosslinked networks at an interface. Such polymers, whether saturated or unsaturated can be substituted with functional groups for subsequent chemistry or crosslinking. (See, examples 11a-c.) For instance, various pyridinyl-terminated polyalkylene oxide ligand components, and corresponding nanoparticulate composites, are used for interfacial assembly, as provided herein, and described in co-pending United States application serial no. 10/643,015 and International application no. PCT/US03/25710 filed on Aug. 18, 2003, each of which is incorporated herein by reference in its entirety. A qualitative depiction of the effect of ligand size on interfacial packing density is shown below (FIG. 5, curvature exaggerated for illustrative purposes), where the nanoparticle density decreases with increasing molecular weight (i.e., radius of gyration) of the polymer on the nanoparticle surface.

Example 11a

Figure 6:
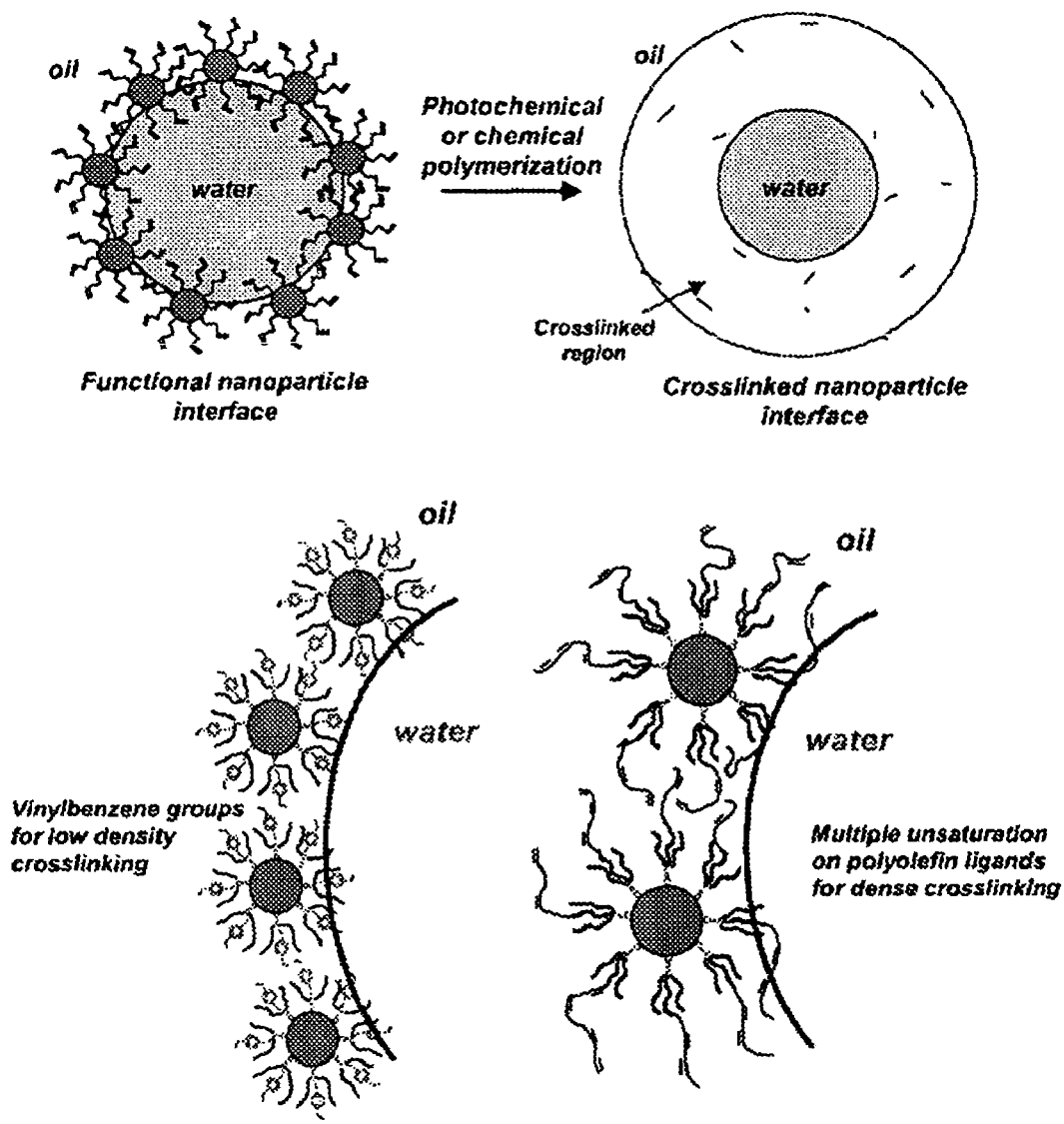
FIG. 6. Schematic illustration of interfacial crosslinking for particle formation (top); higher density capsules are expected with increasing number of available crosslinking sites (bottom).

Crosslinkable interfaces. Functionalized ligands on interfacially assembled nanoparticles are amenable to crosslinking chemistry, either by photochemical or conventional solution methods. For instance, nanoparticles covered with functional ligands can be used for interfacial assembly to provide a nanoparticle scaffold setup for photochemically induced interparticle crosslinking through the unsaturated moieties. The extent of unsaturation affects the ultimate crosslinking density of the interfacial material. The extent of olefin functionalization can be controlled to include 1, 2, or 3 double bonds per ligand, or many double bonds (about 10-about 50) per polymer ligand. This concept is illustrated in FIG. 6 for the general case and for the specific case of nanoparticles functionalized with vinylbenzyl moieties and various unsaturated polyolefins. Due to the very large difference in nanoparticle concentration in the interfacial region vs. the bulk solution, crosslinking at the interface influences the chemistry upon irradiation. Conventional radical initiators or sensitizers may be used to accelerate interfacial crosslinking by thermal or photochemical methods, either in the oil phase using, for example, conventional azo or peroxide initiators, or in water phase using, for example, the water-soluble azo initiator commercially known as "V-50", or 2,2'-azobis(2-amidinopropane).

Example 11b

Preparation of Vinyl benzyl-di-n-octylphosphine oxide CdSe: TOPO-covered nanocrystals were prepared as described above were dispersed in 25 mL anhydrous pyridine and heated at 60° C. overnight. The pyridine was partially removed under reduced pressure to give a viscous solution. The nanocrystals were precipitated into hexane and centrifugated. The supernatant was discarded, and the precipitate (ca. 40 mg CdSe nanocrystals) was stirred as a suspension in freshly distilled, dry THF. para-vinyl benzyl-DOPO (ca. 300 mg) was added, and the suspension was stirred for several hours at 55° C., during which time the mixture became homogenous. Most of the THF was removed by distillation, and the remaining solution was twice precipitated with anhydrous methanol and centrifuged. The supernatant was again discarded, and the p-vinyl benzyl-DOPO-covered nanocrystals were dissolved in toluene (ca. 5 mL).

Example 11c

Preparation of Cross-linked CdSe Nanoparticles Assemblies. Vinyl benzene functionalized CdSe nanoparticles were prepared as described previously and dispersed in toluene. This solution was introduced to an aqueous solution of 2,2'-azobis(2-(2-imidazolin-2-yl)propane) dihydrochloride (Wako VA-044), to give nanoparticle assembly at the oil-water interface. The system was sealed under nitrogen and heated to 60° C. for 6 hours to afford a membrane of crosslinked nanoparticles at the toluene-water interface.

Example 12

Figure 7:
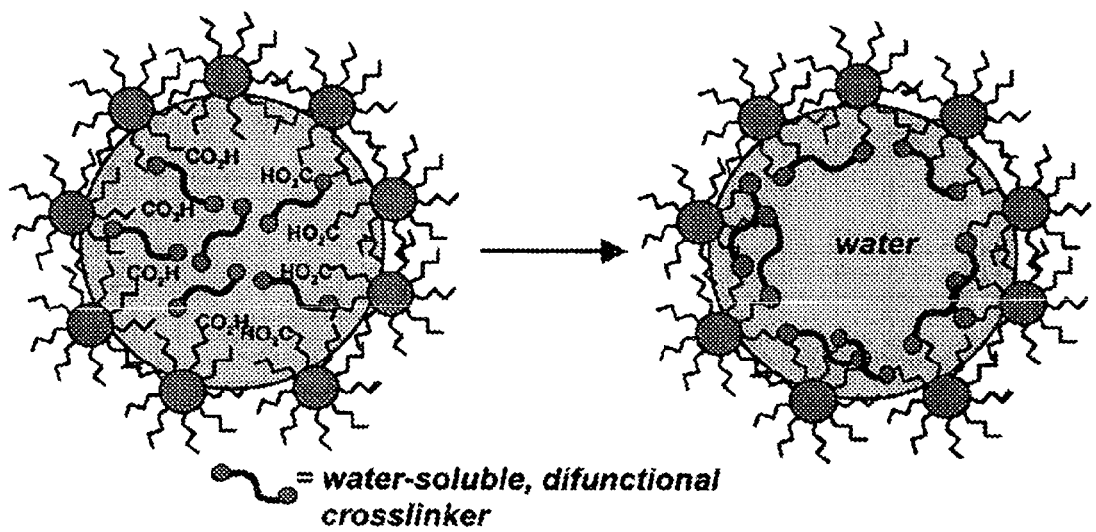
FIG. 7. Multifunctional molecules trapped in the water phase reacting with the nanoparticle ligands at the interface.
Figure 8:
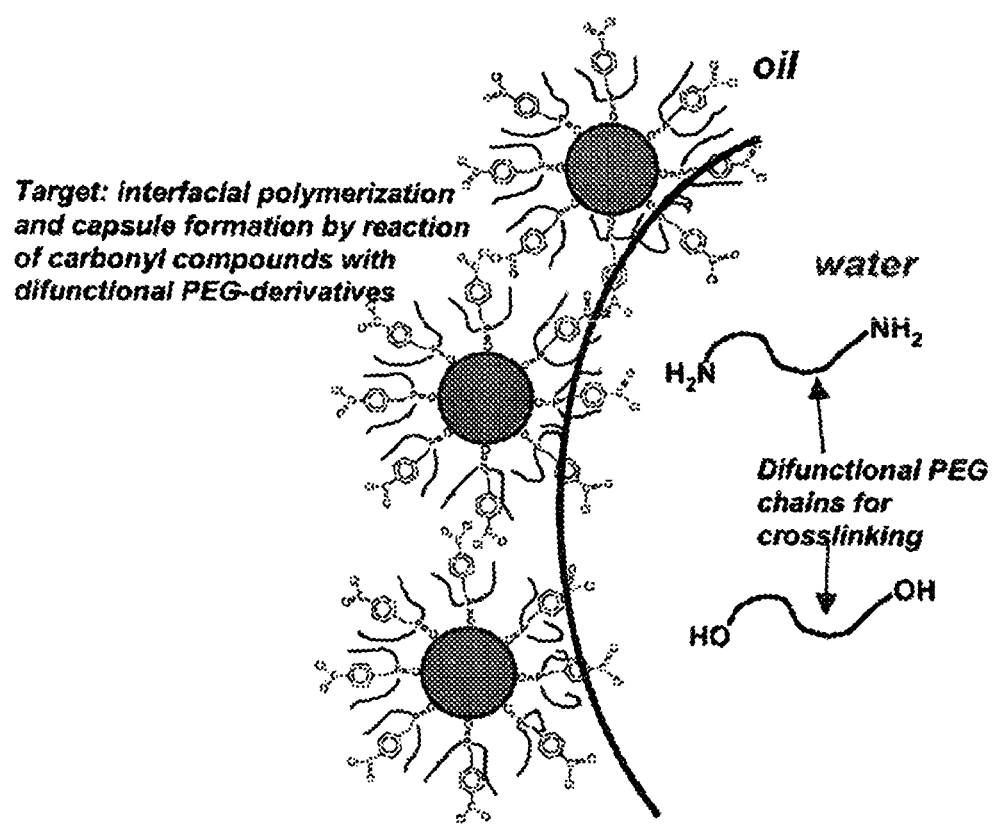
FIG. 8. Interfacial polymerization of water soluble PEG-diols and diamines with interfacial particles.

Capsule formation. Chemical crosslinking of multifunctional reagents introduced into the dispersed phases of these systems are utilized for the preparation of capsules with a wide variety of properties by simply changing the nature of the multifunctional compounds in the dispersed phase. For instance, water-soluble difunctional molecules in a dispersed water phase can promote crosslinking from the "inside" of the interface, as illustrated in FIG. 7. For instance, nanoparticles are encapsulated by phosphine oxide ligands bearing carboxylic acids or acid chlorides in a process related to classic interfacial polymerization, where the carbonyl-based compounds react with a poly or difunctional cross-linking moiety: such as but not limited to $\alpha,\omega$-diols or diamines of polyethylene glycol (PEG) to afford polyester or polyamide covered capsules (FIG. 8). Embodiments with adsorbed PEG can prevent fouling of the nanopores by non-selective adsorption of proteins in biological environments. An oil/organic dispersed phase with corresponding oil soluble or hydrophobic difunctional cross-linking agents can also be used, analogously. This interfacial approach affords capsules of tunable hydrophilicity, swellability, and degradability, where these properties depend on chemical structure (e.g., polyamides or polyesters), and on the molecular weight of the difunctional reagents used for crosslinking.

Example 13a

Encapsulation of materials. The results presented in several preceding examples demonstrate the ability to encapsulate water-soluble fluorescent dyes within nanoparticle assemblies and to introduce a gel into the dispersed water phase, and illustrate a feasible route for encapsulating any water-soluble compound or component. Conversely, this approach can be used to assemble particles on an organic fluid dispersed in water. Hence, a variety of oil- or water-soluble macromolecules may be encapsulated.

Figure 9:
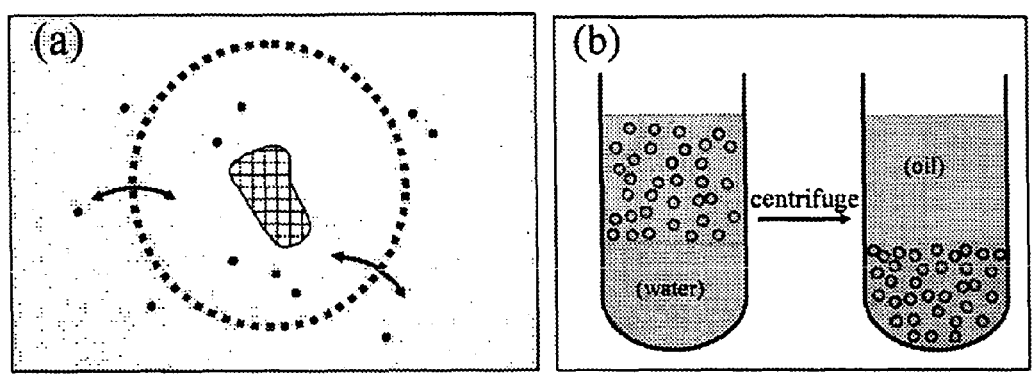
FIG. 9A-B. (A) Schematic illustration of a selectively permeable capsule that allows diffusive exchange of small molecules but retains (or excludes) larger ones. (B) Process of transferring self-assembled capsules to a different solvent. In this example, water-filled capsules constructed in oil are transferred directly to water.

As the coated droplet (capsule) is mechanically robust, the suspension fluid component can be exchanged with one that is identical to the fluid or solvent component within the capsule. With the fluid-fluid interface removed, molecular components within the dispersed phase diffuse out of the capsule. The rate of diffusive escape is determined by capsule porosity and the chemical potential gradient thereacross (FIG. 9A). The porosity of the shell (hence, the rate of diffusive release) is controlled during fabrication and by post-fabrication modification. As an example of nanometer-scale control of permeability, consider the encapsulation of water-soluble drugs, such as adriamycin (a.k.a., doxorubicin, below), an important agent in cancer therapeutics, but one well-known for its harmful side-effects. New encapsulation strategies for such drugs, as represented by the capsules presented herein, may be helpful in controlling the rate of drug release, and avoiding the "burst" in drug levels often responsible for deleterious side-effects.

Example 13b

Preparation of Doxorubicin Hydrochloride Encapsulated CdSe Nanoparticle Vesicles. To a solution (c.a. 2 mL) of TOPO-covered or vinyl benzyl-di-n-octylphosphine oxide-covered CdSe nanoparticles in toluene, one drop of an aqueous doxorubicin hydrochloride solution (c.a. 0.1 mM) was added. The two-phase mixture was mechanically agitated or sonicated to form doxorubicin hydrochloride encapsulated CdSe nanoparticle vesicles.

Example 13c

To remove the interface, capsules can, for example, be transferred from oil to water by centrifugation, as illustrated in FIG. 9B using known techniques. Here, aqueous droplets containing material to be encapsuled were dispersed in oil whose mass density was less than that of water. After coverage of the interface with micro-particles that were subsequently fixed together (electrostatically, by van der Waals, or by sintering), an aliquot of the coated droplets was placed atop water and the sample was placed in a centrifuge. The capsules were dragged across the interface into the aqueous phase. The same centrifugation process was used to transfer encapsulated oil droplets from an aqueous exterior solvent into oil. In both cases, microscope observations proved that particles smaller than the interstices in the shell were able to permeate the capsule. An alternative approach (when chemical contamination is not an issue) is to dissolve the interface by addition of a mutually miscible solvent.

Example 14

Capsule Characterization. The mechanical toughness of the capsules is characterized by measuring the maximum shear stress (yield stress) that can be applied to the capsules before rupture. Understanding and controlling the yield stress is essential to avoid (or, alternatively, to promote) rupture-induced release of an encapsulated material. Such tests apply simple shear (shear rates up to $10^3$ $s^{-1}$) simultaneously with three-dimensional optical confocal imaging Yield stress are measured by encapsulating fluorescent beads, then measuring the maximum stress that can be applied without rupturing the capsules and releasing the beads. The modulus and yield stress of individual capsules are measured directly by pulling with an elastic rod of known spring constant. Hydraulic micromanipulators equipped with glass pipettes and mounted into an optical microscope are used as the mechanical probe. The deflection of the elastic rod (or pipette) indicates the applied force; the resulting distortion of the capsule's shape (the strain) is determined by analyzing optical microscope images.

Example 15a

Figure 10:
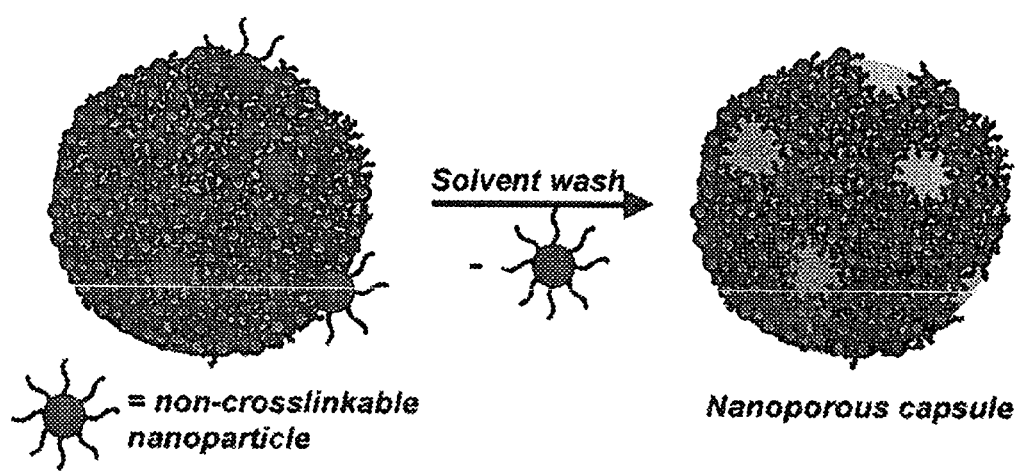
FIG. 10. Synthesis of nanoporous capsules by removal of non-crosslinked nanoparticles from the interface.

Variable pore sizes for controlled diffusive release. The crosslinking chemistry described above can provide capsules with pores of controlled size and density. The ability to introduce pores of well-defined size and number into the robust, tough membranes of this invention offers tremendous flexibility in controlling permeability. For example, the ability of macromolecules (e.g., drugs, proteins, and DNA) to translocate through nanometer-sized pores is known to depend on the molecular weight of the macromolecule (Hoagland, D. A. and coworkers, Science, 2002, 987-990. Nanometer-sized pores of controlled size are incorporated into the capsules using inert adsorbed particles as templates (FIG. 10): for instance, by incorporating a percentage of non-functional (i.e., non-crosslinkable) nanoparticles at the interface. In such embodiments, the covalent bonding of the crosslinking reactions bypass the non-functional nanoparticles, which are later removed by washing, to give nanopores on the surface of the crosslinked material. (See, Example 15b, below.) The number of pores can be tuned or predetermined by adjusting the percentage of non-reactive or non-crosslinkable nanoparticles at the interface, and the size of the pores by adjusting the size of the ligands attached or complexed to the nanoparticles.

Larger pores of controlled size can be incorporated by addition of larger, inert particles to be removed after capsule preparation. Capsules with 20-nm pores have been a long-standing goal for encapsulating and immunoisolating cells for treatment of diabetes, cancer and other illnesses. Upon implantation of living cells into a host, pores of this size protect the cells from the host's immune response, yet allow exchange of nutrients and secreted chemicals. Existing approaches to fabricating immunoisolating capsules may result in a distribution of pore sizes too broad to be effective, or may require laborious lithographic processing, one capsule at a time. The present approach offers significantly greater control of the permeability of the encapsulating membrane.

Example 15b

Preparation of Porous Cross-linked CdSe Nanoparticles Assemblies. Vinyl benzene functionalized CdSe nanoparticles were prepared as described previously and dispersed in toluene. This solution was introduced to an aqueous solution of 2,2'-azobis(2-(2-imidazolin-2-yl)propane) dihydrochloride (Wako VA-044), to give nanoparticle assembly at the oil-water interface. A toluene solution of TOPO-covered CdSe nanoparticle of a larger size was added to the assembly mixture. The assembly was allowed to stand so as to allow for partial displacement of the smaller vinyl benzene functionalized CdSe nanoparticles and subsequent phase-seperation to occur. The system was sealed under nitrogen and heated to 60° C. for 6 hours to afford a membrane of cross-linked nanoparticles at the toluene-water interface. The non-functional TOPO-covered CdSe nanoparticle were removed by multiple washes with toluene to give a porous, cross-linked assembly of nanoparticles at the oil-water interface.

Example 16

Figure 11:
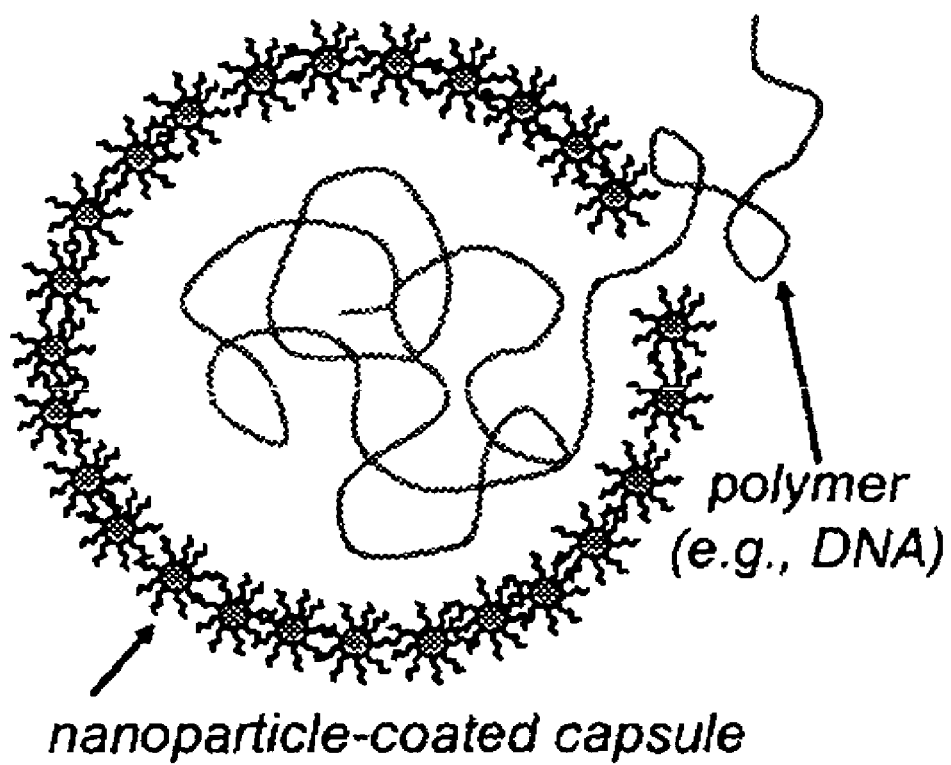
FIG. 11. Illustration of a polymer such as DNA escaping from the interior of a capsule through a single nanometer-sized pore.

Polymer and DNA encapsulation. This example illustrates the encapsulation of polymeric materials, ranging from synthetic polymers to naturally occurring macromolecules such as DNA (FIG. 11). Escape of a polymer chain from a well-defined nanoscale pore is monitored as a function of time, pore size, polymer molecular weight, and chemical potential gradient across the capsule membrane. An initial focus is on fluorescently labeled DNA and proteins, encapsulated within water droplets, and fluorescently labeled synthetic polymers, such as poly(ethylene oxide) and polystyrene. The concentration of entrapped chains can be monitored by the fluorescence intensity, and diffusion of the macromolecule out of the capsule by fluorescence optical and confocal microscopies. The chemical and electrostatic interactions between the translocating polymer and the pore can be varied by the use of ligands of various charge, and the choice of nanoparticles (i.e., electrically conducting or insulating). Such control affords unique opportunities to understand diffusion where the entropy of the chain is an impediment to escape.

Example 17

Electronic and optical properties of capsules. Owing to the range of highly controllable and robust electronic and optical properties of the nanoparticles of this invention, capsules and films formed using the present methodologies exhibit a broad range of properties. Consider bright photoluminescence, which allows for the preparation of capsules that are color-coded according to their contents. Moreover, the spacing of the particles dictates the extent of inter-particle electronic and magnetic coupling. When particles lie within approximately 1 nm of one another, their luminescence color can red-shift. Moreover, if the particles are metallic, then they can undergo a reversible transition from electrically insulating to conducting as the particles move to within approximately 0.5 nm of one another. The optical properties of a film or capsule are sensitive to the inter-particle spacings. With the present invention, the spacing between particles can be varied by mechanical stretching, heating, or solvent-induced swelling and other techniques known in the art. Accordingly, the nanoparticle-based capsule can also act as a sensor of stress, temperature or chemical environment.

Example 18a

Figure 12:
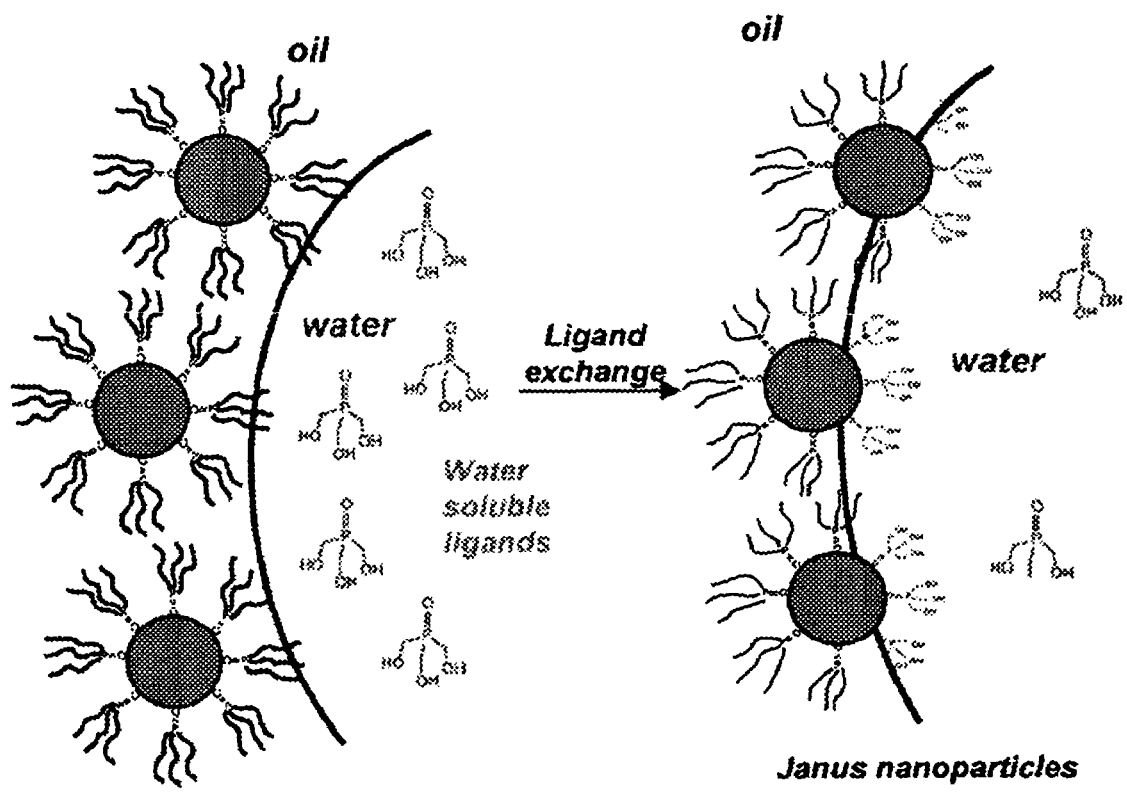
FIG. 12. Formation of Janus nanoparticles by interfacial ligand exchange. Refer also to FIG. 4.
Figure 13:
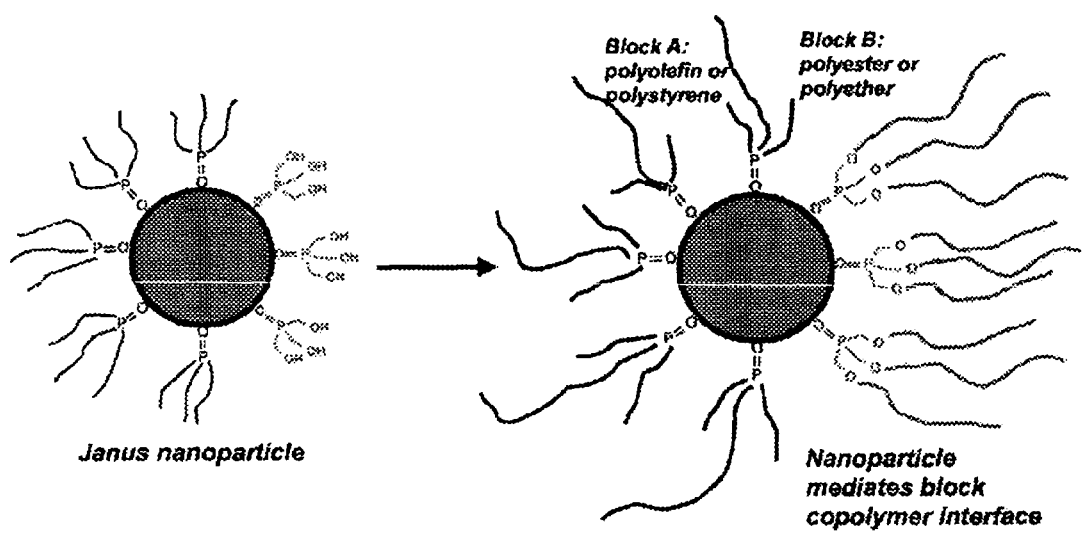
FIG. 13. The use of Janus nanoparticles as multifunctional initiators to give block copolymers containing an interfacial nanoparticle junction.

Ligand exchange chemistries. The interfacial relationships associated with this invention allow new chemistry to be conducted on nanoparticles: for example, as mentioned above, the preparation of Janus nanoparticles having two distinct functional groups associated with the particle to give two distinct chemical "faces" to the particulate structure. The oil-water nature of an interface leads to the preparation of amphiphilic nanoparticles, where one face is hydrophobic and the other hydrophilic. Such orthogonal functionalization allows conversion of the janus nanoparticles to particles covered or complexed with different polymers. The nanoparticles can then be used, for instance, to define the interfacial junction point of a block copolymer. An example is depicted in FIG. 12, where hydrophilic ligands (containing three hydroxy groups) attach to the nanoparticles at the interface. Isolation of these nanoparticles followed by polymerization can provide, for instance, hydrophobic polymers (e.g., polyolefins) from one face, and hydrophilic polymers (e.g., polyesters or polyethers) from the other face (FIG. 13).

Example 18b

Figure 14:
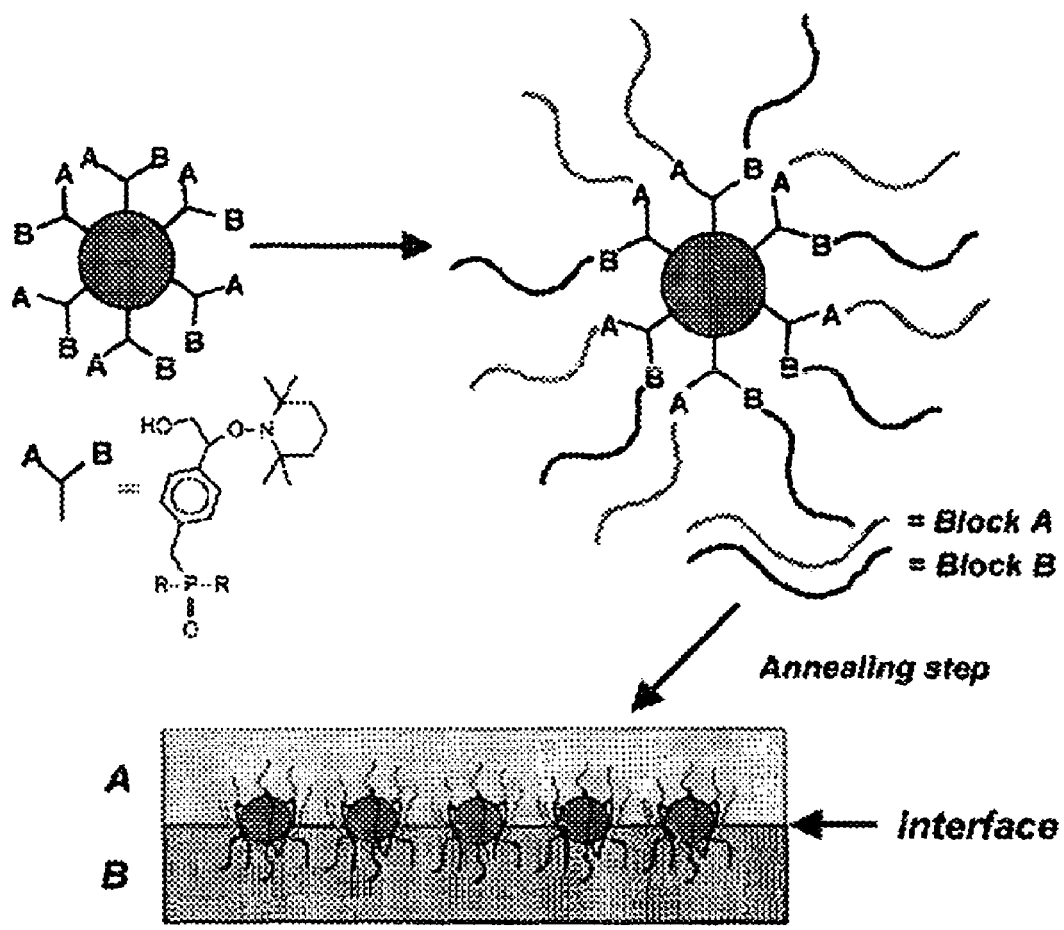
FIG. 14. Nanoparticle-labeled interface, prepared by polymerization of two different polymers from Janus nanoparticles.

Such Janus nanoparticles at an oil-water interface could also be associated with two different types of functionality: such as difunctional molecules bound to the nanoparticle surface, where the two functionalities are different, but emanate from one ligand site. The schematic illustration of FIG. 14 shows a phosphine oxide ligand with, for instance, 1) a nitroxide moiety (e.g., to mediate styrenic polymerizations), and 2) an alcohol (e.g., to initiate lactone polymerization for the preparation of polyesters).

Using a preferred nanoparticle, composite materials of CdSe nanoparticles, polystyrene, and a polyester such as poly($\epsilon$-caprolactone) are prepared. By this route, block copolymers having CdSe nanoparticle junction points are also prepared. These and other polymers can be used for self-assembly in the bulk and as compatibilizing agents in mixtures. A unique advantage of the copolymers is that the photoluminescence of the nanoparticles provides distinct markers of the junction points.

Example 19a

A 7 wt.-% solution of polystyrene ($M_w$=76 kg/mol, Polymer Source Inc.) in chloroform containing 1% CdSe nanoparticles (core diameter: 4.0 nm) stabilized with tri-n-trioctylphosphine oxide (TOPO) was prepared. To form the breath figure structure, a 30 µL drop of the solution was placed on a cover glass in a humidity controlled chamber and the solvents were allowed to evaporate at room temperature and 80% relative humidity. The humidity was controlled using nitrogen bubbled through a flask of distilled water at 30° C. and was measured with a commercially available hygrometer.

Example 19b

Transmission Electron Microscopy (TEM). The porous films were embedded in epoxy and cured for 12 hrs at 60° C. 50-80 nm thick cross-sections were cut using a Leica Ultracut microtome equipped with a diamond knife. Bright field TEM was performed on unstained samples using a JEOL 200CX electron microscope operated at 200 kV.

Example 19c

Laser Scanning Confocal Microscope (LSCM). The laser scanning confocal microscope images were taken on a Leica TCS SP2 LSCM with an oil-emersion objective and Ar-laser excitation (excitation: 488 nm, detection: 590 nm). The fluorescence from the CdSe nanoparticles is observed in red.

Example 19d

Scanning Electron Microscopy (SEM). Secondary electron and Cathodoluminescence (CL) SEM was performed using a LEO 1530 Gemini instrument equipped with a field emission cathode. The acceleration voltage was 0.8 and 7 kV, respectively. The CL is detected at an angle of 30° and is sensitive to a wavelength range of $\lambda$~185-850 nm.

Example 20

In order to further support the interfacial segregation of nanoparticles in the breath figures, and to elucidate their sub-structure, transmission electron microscopy was performed on thin cross sections of the polystyrene films. A thin black line observed in the micrograph is attributed to the nanoparticle assembly produced during breath figure formation at the liquid-liquid interface. The 5-7 nm thickness of the lines corresponds to a monolayer of CdSe-TOPO nanoparticles, as calculated from the core diameter and the ligand length.

Example 21

SEM images also yield evidence for the selective nanoparticle assembly within the holes. A bright rim is seen around the opening of the cavities, which originates from the CdSe nanoparticles, which possess the highest secondary electron yield in the sample. Some of the cavities exhibit either a rough interior which may be attributed to agglomeration of the CdSe nanoparticles (as also observed by TEM), or incomplete coverage. The latter is in agreement with the fluorescence microscopy image. These defects, however, lead us to believe that the observed features in the SEM images arise from the nanoparticle assembly within the breath figure holes.

To probe the CdSe nanoparticles independently, cathodoluminescence—predominantly found around the breath figure holes—was monitored. The rings appear fuzzy as not only particles at the rim but also those deeper inside the polymer film become visible, owing to the larger penetration depth of the 7 kV primary electrons.

Example 22

A fluorescence confocal microscope digital image of air/toluene and toluene/water interfaces with 4.6±0.2 nm diameter tri-n-octylphosphine oxide (TOPO)-stabilized CdSe nanoparticles in toluene shows nanoparticle assembly at the toluene/water interface, while there is no noticeable assembly at the toluene/air interface. The nanoparticles self-assemble so as to form a separating layer between the water and toluene. Studies of dried droplets with atomic force microscopy, transmission electron microscopy, and in situ studies by small-angle X-ray scattering indicate that the nanoparticles form a nearly close-packed monolayer with liquidlike ordering.

Example 23a

The dense packing of the ligand-covered nanoparticles at the fluid/fluid interface suggests stabilizing the assembly by cross-linking the ligands. CdSe nanoparticles with a core diameter of 2.9±0.2 nm and covered with reactive vinylbenzene moieties were prepared as described previously and dispersed in toluene. This solution was introduced to an aqueous solution of 2,2'-azobis(2-(2-imidazolin-2-yl)propane) dihydrochloride (Wako VA-044), to give nanoparticle assembly at the planar oil/water interface. The system was sealed under nitrogen and heated to 60° C. for 6 h to afford a membrane of cross-linked nanoparticles at the toluene/water interface. The membrane was removed from the interface by pipet and suspended in toluene.

Example 23b

A three-dimensional confocal fluorescence microscope image shows a sheet suspended in toluene (rotated to view at three different angles). The surface area of the sheet is on the order of 1 cm². The crumpled morphology observed may result from shear stresses during manipulation with the micropipet. The fluorescence emission (excitation: 488 nm, detection: 540 nm) arises from the nanoparticles, unchanged before and after assembly and cross-linking. The observation of a structurally intact membrane floating freely in toluene demonstrates that the ligands attached to the nanoparticles cross-linked into a continuous, elastic membrane. This membrane, while clearly observable by photoluminescence, is invisible in a transmission optical microscope due to its ultrathin nature.

Example 23c

The morphology of the crumpled sheets provides insight into their elastic properties. The pronounced ridges observed in the confocal images are similar to those seen in macroscopic crumpled elastic sheets such as paper or aluminum foil. Elasticity theory characterizes this elastic sheet by an area-expansion modulus G and a bending modulus κ. If the membrane is composed of an isotropic material, then $(\kappa/G)^{1/2}$ is approximately equal to the membrane thickness. The ratio of κ/G also determines the morphology of the crumpled sheet and can be measured by comparing the typical curvature, $C_o$, and the length, L, of the ridges as $$C_o \approx \left(\frac{1}{L}\right)\left(\frac{L}{(\kappa/G)^{1/2}}\right)^{1/3}$$

From the confocal images, many $C_o$ and L pairs were measured to give $(\kappa/G)^{1/2}$ from 2 to 7 nm, comparable to the membrane thickness (~5 nm). The deformation is consistent with that of a uniform elastic sheet. An upper bound to k can be obtained by modeling the membrane as a ~5-nm thick layer of polystyrene, which yields is $\kappa \approx 10^5 k_B T$. While this is an overestimate, it is consistent with the fact that no thermal undulations of the membrane were observed, indicating that κ is at least $10^5 k_B T$.

Example 23d

Permeable and robust sheets of the type shown here have great potential as diffusion barriers. Following sheet formation at the toluene/water interface as described above, a droplet of an aqueous solution of sulforhodamine-B was placed on top of the membrane. The curvature of the membrane arises from its contact with the side walls of the tube and the energies of the toluene/water, toluene/wall, and water/wall interfaces. Additional dye solution was then added, and the tube was tapped vigorously to spread the dye across the membrane and to remove toluene trapped between the dye and the membrane. This resulted in a decreased curvature of the membrane but no convective transport of the dye across the membrane. After 12 min the dye had diffused across the nanoparticle membrane and into the water phase.

It should be noted that the diffusion front of the dye in the water is fairly sharp, indicating an absence of convection current in the water phase. In control experiments using non-crosslinked assemblies of CdSe nanoparticles, the dye solution penetrated the nanoparticle assembly by convection, immediately dispersing the sulforhodamine-B in the water at the base of the tube. These results point to the robust barrier properties of the nanoparticle membrane and their ability to prevent convective mixing. They also show that the membrane is permeable, yet may serve to retard or suppress the diffusion of larger molecules across the layer.

Example 23e

Cross-linking of the ligands can also be used to stabilize nanoparticle assembly on the interface of droplets and encapsulation of water droplets by a shell of cross-linked nanoparticles. Subsequent centrifugation and washing with pure toluene caused some of the cross-linked shells to crack, as observed under confocal microscopic imaging. Nevertheless, the integrity of the assembly is maintained, showing the impact of ligand cross-linking in promoting the mechanical and structural stability of the assemblies. As such, interfacial cross-linking at droplet surfaces enables the encapsulation of water-soluble or oil-soluble materials inside the resulting nanocontainers. By varying the concentration of the nanoparticulates and/or reactive moieties, it is possible to control the permeability and strength of such nanostructured membranes and capsules.

While the principles of this invention have been described in connection specific embodiments, it should be understood clearly that these descriptions are added only by way of example and are not intended to limit, in any way, the scope of this invention. For instance, the present invention can include, more specifically, various other nanoparticulate composites (e.g., metal or metallic substrates and organic ligands) as can be prepared as described herein or by straightforward modifications of known synthetic techniques, depending upon choice of substrate or ligand, as would be understood by those skilled in the art made aware of this invention. Other advantages, features and benefits will become apparent from the claims hereinafter, likewise as understood by those skilled in the art.

We claim:

1. A system for interfacial nanoparticulate assembly, said system comprising:
   a first fluid component;
   a second fluid component dispersed by said first fluid component, said first and second fluid components at least partially immiscible one with the other, said immiscibility defining a fluid component interface; and
   nanoparticulates assembled at said fluid component interface, at least one of said nanoparticulates comprising a substrate and a ligand component.

2. The system of claim 1 wherein said substrate is selected from a metal, a metal alloy, a metal oxide, a metal selenide, a metal sulfide and a combination thereof.

3. The system of claim 1 wherein said ligand component comprises a hydrophobic moiety.

4. The system of claim 3 wherein said moiety is selected from pyridine, tri-n-octylphosphine, vinylbenzene and a combination thereof.

5. The system of claim 1 wherein second fluid component comprises a reagent reactive with said ligand component.

6. The system of claim 5 wherein said ligand component comprises a vinylbenzene and said reagent is a free radical initiator.

7. The system of claim 5 wherein said ligand comprises a carboxylate and said reagent is selected from a polyfunctional amine and a polyfunctional alcohol.

8. The system of claim 1 wherein said first fluid component is hydrophobic, said second fluid component is aqueous and dispersed in said first fluid component, and said assembled nanoparticulates comprise a substantially spherical capsule at said fluid component interface.

9. The system of claim 8 wherein said assembled nanoparticulates encapsulate said second fluid component upon removal of said first fluid component.

10. The system of claim 8 wherein said second fluid component further comprises a therapeutic agent.

11. The system of claim 8 wherein said second fluid component is aqueous and comprises a hydrophilic ligand.

12. The system of claim 11 wherein at least one of said nanoparticulate ligand and said hydrophilic ligand comprises a reactive functionality.

13. The system of claim 1 wherein said first fluid component comprises a polymer-solvent solution and said second fluid component comprises condensed atmospheric moisture, said condensate dispersed in an array on said solution surface.

14. The system of claim 13 wherein said assembled nanoparticulates define a cavity in said first fluid component upon removal of said second fluid component.

15. The system of claim 1 wherein said nanoparticulates comprise first and second nanoparticulates, said first nanoparticulates diametrally dimensioned less than said second nanoparticulates.

16. A system for interfacial nanoparticulate assembly, said system comprising:
   a first fluid component;
   a second fluid component dispersed by said first fluid component, said first and second fluid components at least partially immiscible one with the other, said immiscibility defining a fluid component interface; and
   nanoparticulates assembled at said fluid component interface, at least one of said nanoparticulates comprising a substrate and a ligand component comprising a hydrophobic moiety selected from pyridine, tri-n-octylphosphine, vinylbenzene and a combination thereof.

17. The system of claim 16 wherein said substrate is selected from a metal, a metal alloy, a metal oxide, a metal selenide, a metal sulfide and a combination thereof.

18. The system of claim 16 wherein second fluid component comprises a reagent reactive with said ligand component.

19. The system of claim 18 wherein said ligand component comprises a vinylbenzene and said reagent is a free radical initiator.

20. The system of claim 18 wherein said ligand comprises a carboxylate and said reagent is selected from a polyfunctional amine and a polyfunctional alcohol.

21. The system of claim 16 wherein said first fluid component is hydrophobic, said second fluid component is aqueous and dispersed in said first fluid component, and said assembled nanoparticulates comprise a substantially spherical capsule at said fluid component interface.

22. The system of claim 21 wherein said assembled nanoparticulates encapsulate said second fluid component upon removal of said first fluid component.

23. The system of claim 21 wherein said second fluid component further comprises a therapeutic agent.

24. The system of claim 21 wherein said second fluid component is aqueous and comprises a hydrophilic ligand.

25. The system of claim 24 wherein at least one of said nanoparticulate ligand and said hydrophilic ligand comprises a reactive functionality.

26. The system of claim 16 wherein said first fluid component comprises a polymer solvent solution and said second fluid component comprises condensed atmospheric moisture, said condensate dispersed in an array on said solution surface.

27. The system of claim 26 wherein said assembled nanoparticulates define a cavity in said first fluid component upon removal of said second fluid component.

28. The system of claim 16 wherein said nanoparticulates comprise first and second nanoparticulates, said first nanoparticulates diametrally dimensioned less than said second nanoparticulates.

29. A system for interfacial nanoparticulate assembly, said system comprising:
   a first fluid component comprising a polymer-solvent solution;
   a second fluid component comprising condensed atmospheric moisture and dispersed by said first fluid component, said first and second fluid components at least partially immiscible one with the other, said immiscibility defining a fluid component interface, said condensate dispersed in an array on said first component solution surface; and
   nanoparticulates assembled at said fluid component interface, at least one of said nanoparticulates comprising a substrate and a ligand component.

30. The system of claim 29 wherein said assembled nanoparticulates define a cavity in said first fluid component upon removal of said second fluid component.

31. The system of claim 29 wherein said nanoparticulates comprise first and second nanoparticulates, said first nanoparticulates diametrally dimensioned less than said second nanoparticulates.

* * * * *